US012702552B2

(12) United States Patent
Goldberg

(10) Patent No.: US 12,702,552 B2
(45) Date of Patent: Aug. 11, 2026

(54) LOADING APPARATUS FOR LOADING A PROSTHETIC HEART VALVE INTO A DELIVERY APPARATUS

(71) Applicant: Edwards Lifesciences Corporation, Irvine, CA (US)

(72) Inventor: Eran Goldberg, Nesher (IL)

(73) Assignee: Edwards Lifesciences Corporation, Irvine, CA (US)

( * ) Notice: Subject to any disclaimer, the term of this patent is extended or adjusted under 35 U.S.C. 154(b) by 863 days.

(21) Appl. No.: 18/048,354

(22) Filed: Oct. 20, 2022

(65) Prior Publication Data

US 2023/0061356 A1 Mar. 2, 2023

Related U.S. Application Data

(63) Continuation of application No. PCT/US2021/028069, filed on Apr. 20, 2021.

(60) Provisional application No. 63/013,146, filed on Apr. 21, 2020.

(51) Int. Cl.
*A61F 2/95* (2013.01)
*A61F 2/24* (2006.01)

(52) U.S. Cl.
CPC .......... *A61F 2/2436* (2013.01); *A61F 2/9525* (2020.05)

(58) Field of Classification Search
CPC .................................................... A61F 2/9525
See application file for complete search history.

(56) References Cited

U.S. PATENT DOCUMENTS

| | | | | |
|---|---|---|---|---|
| 519,297 | A | | 5/1894 | Wanek et al. |
| 4,035,849 | A | | 7/1977 | Angell et al. |
| 4,592,340 | A | | 6/1986 | Boyles |
| 4,830,003 | A | * | 5/1989 | Wolff ........................ A61F 2/86 606/191 |
| 4,955,895 | A | | 9/1990 | Sugiyama et al. |
| 4,994,077 | A | | 2/1991 | Dobben |
| 5,059,177 | A | | 10/1991 | Towne et al. |
| 5,176,698 | A | | 1/1993 | Burns et al. |
| 5,192,297 | A | | 3/1993 | Hull |
| 5,266,073 | A | | 11/1993 | Wall |
| 5,325,845 | A | | 7/1994 | Adair |
| 5,358,496 | A | | 10/1994 | Ortiz et al. |
| 5,411,552 | A | | 5/1995 | Andersen et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Jacqueline Woznicki
(74) *Attorney, Agent, or Firm* — Klarquist Sparkman LLP

(57) ABSTRACT

A loading apparatus including an outer body, a guide tube, and an annular loading member is disclosed. As one example, the outer body includes an inner conical bore that narrows in diameter from a distal end to a proximal end portion of the outer body and the guide tube includes a distal portion arranged within the proximal end portion of the outer body and a proximal portion extending outward from the outer body. The annular loading member can include a ring portion and a plurality of arms extending outward, in an axial direction relative to a central longitudinal axis of the loading apparatus, from the ring portion, the ring portion coupled to an inner surface of the distal portion of the guide tube.

17 Claims, 10 Drawing Sheets

(56) References Cited

U.S. PATENT DOCUMENTS 5,554,185 A 9/1996 Block et al.
5,591,195 A 1/1997 Taheri et al.
5,599,305 A 2/1997 Hermann et al.
5,632,760 A 5/1997 Sheiban et al.
5,639,274 A 6/1997 Fischell et al.
5,725,519 A * 3/1998 Penner .................. A61F 2/9525 606/1
5,728,068 A 3/1998 Leone et al.
5,749,890 A 5/1998 Shaknovich
5,782,809 A 7/1998 Umeno et al.
5,824,044 A 10/1998 Quiachon et al.
5,840,081 A 11/1998 Andersen et al.
5,908,405 A 6/1999 Imran et al.
5,916,147 A 6/1999 Boury
5,944,690 A 8/1999 Falwell et al.
5,961,536 A 10/1999 Mickley et al.
5,968,068 A 10/1999 Dehdashtian et al.
6,019,777 A 2/2000 Mackenzie
6,027,510 A 2/2000 Alt
6,033,381 A 3/2000 Kontos
6,143,016 A 11/2000 Bleam et al.
6,162,208 A 12/2000 Hipps
6,168,614 B1 1/2001 Andersen et al.
6,174,327 B1 1/2001 Mertens et al.
6,217,585 B1 4/2001 Houser et al.
6,235,050 B1 5/2001 Quiachon et al.
6,251,092 B1 6/2001 Qin et al.
6,379,372 B1 4/2002 Dehdashtian et al.
6,383,171 B1 5/2002 Gifford et al.
6,454,799 B1 9/2002 Schreck
6,458,153 B1 10/2002 Bailey et al.
6,461,382 B1 10/2002 Cao
6,471,672 B1 10/2002 Brown et al.
6,500,147 B2 12/2002 Omaleki et al.
6,514,228 B1 2/2003 Hamilton et al.
6,527,979 B2 3/2003 Constantz et al.
6,579,305 B1 6/2003 Lashinski
6,582,462 B1 6/2003 Andersen et al.
6,652,578 B2 11/2003 Bailey et al.
6,730,118 B2 5/2004 Spenser et al.
6,733,525 B2 5/2004 Yang et al.
6,764,504 B2 7/2004 Wang et al.
6,767,362 B2 7/2004 Schreck
6,830,584 B1 12/2004 Seguin
6,893,460 B2 5/2005 Spenser et al.
6,908,481 B2 6/2005 Cribier
7,011,094 B2 3/2006 Rapacki et al.
7,018,406 B2 3/2006 Seguin et al.
7,018,408 B2 3/2006 Bailey et al.
7,137,993 B2 11/2006 Acosta et al.
7,276,084 B2 10/2007 Yang et al.
7,318,278 B2 1/2008 Zhang et al.
7,320,702 B2 1/2008 Hammersmark et al.
7,320,704 B2 1/2008 Lashinski et al.
7,374,571 B2 5/2008 Pease et al.
7,393,360 B2 7/2008 Spenser et al.
7,435,257 B2 10/2008 Lashinski et al.
7,510,575 B2 3/2009 Spenser et al.
7,585,321 B2 9/2009 Cribier
7,594,926 B2 9/2009 Linder et al.
7,597,709 B2 10/2009 Goodin
7,618,446 B2 11/2009 Andersen et al.
7,780,723 B2 8/2010 Taylor
7,785,366 B2 8/2010 Maurer et al.
7,959,661 B2 6/2011 Hijlkema et al.
8,029,556 B2 10/2011 Rowe
8,052,750 B2 * 11/2011 Tuval .................... A61F 2/2436 623/2.14
8,167,932 B2 5/2012 Bourang et al.
8,449,606 B2 5/2013 Eliasen et al.
8,475,523 B2 7/2013 Duffy
8,568,472 B2 10/2013 Marchand et al.
8,652,202 B2 * 2/2014 Alon ..................... A61F 2/2433 623/2.11
8,906,081 B2 * 12/2014 Cully ........................ A61F 2/97 623/1.13
8,931,159 B2 * 1/2015 Hillukka ............... A61F 2/2418 623/2.11
9,061,119 B2 6/2015 Le et al.
9,119,716 B2 9/2015 Lee et al.
9,345,573 B2 * 5/2016 Nyuli ...................... A61F 2/962
9,681,969 B2 * 6/2017 Robinson .............. A61F 2/2436
9,795,477 B2 10/2017 Tran et al.
10,368,986 B2 * 8/2019 Gosal .................... A61F 2/2427
11,273,038 B2 3/2022 Tang et al.
11,857,441 B2 * 1/2024 Diedering ................. A61F 2/95
2001/0002445 A1 5/2001 Vesely
2001/0007082 A1 7/2001 Dusbabek et al.
2002/0032481 A1 3/2002 Gabbay
2002/0058995 A1 5/2002 Stevens
2002/0165461 A1 11/2002 Hayzelden et al.
2003/0040792 A1 2/2003 Gabbay
2003/0050694 A1 3/2003 Yang et al.
2003/0120341 A1 6/2003 Shennib et al.
2003/0139795 A1 * 7/2003 Olson ....................... A61F 2/95 623/1.11
2004/0093061 A1 5/2004 Acosta et al.
2004/0133263 A1 7/2004 Dusbabek et al.
2004/0143197 A1 7/2004 Soukup et al.
2004/0186563 A1 9/2004 Lobbi
2004/0186565 A1 9/2004 Schreck
2004/0260389 A1 12/2004 Case et al.
2005/0080474 A1 4/2005 Andreas et al.
2005/0096736 A1 5/2005 Osse et al.
2005/0137689 A1 6/2005 Salahieh et al.
2005/0149160 A1 7/2005 McFerran
2005/0203614 A1 9/2005 Forster et al.
2005/0203617 A1 9/2005 Forster et al.
2005/0245894 A1 11/2005 Zadno Azizi
2006/0025857 A1 2/2006 Bergheim et al.
2006/0167468 A1 * 7/2006 Gabbay ................. A61F 2/2436 623/2.11
2006/0259134 A1 * 11/2006 Schwammenthal .. A61F 2/2436 623/2.11
2006/0282150 A1 12/2006 Olson et al.
2007/0005131 A1 1/2007 Taylor
2007/0073389 A1 3/2007 Bolduc et al.
2007/0088431 A1 4/2007 Bourang et al.
2007/0100356 A1 5/2007 Lucatero et al.
2007/0112422 A1 5/2007 Dehdashtian
2007/0162100 A1 * 7/2007 Gabbay ..................... A61F 2/95 623/1.11
2007/0203575 A1 8/2007 Forster et al.
2007/0219612 A1 9/2007 Andreas et al.
2007/0239254 A1 10/2007 Chia et al.
2007/0244546 A1 10/2007 Francis
2007/0265700 A1 11/2007 Eliasen et al.
2008/0065011 A1 3/2008 Marchand et al.
2008/0103520 A1 5/2008 Selkee
2008/0125853 A1 5/2008 Bailey et al.
2008/0294230 A1 11/2008 Parker
2009/0024428 A1 1/2009 Hudock
2009/0069889 A1 3/2009 Suri et al.
2009/0138079 A1 5/2009 Tuval et al.
2009/0157175 A1 6/2009 Benichou
2009/0192585 A1 7/2009 Bloom et al.
2009/0228093 A1 9/2009 Taylor et al.
2009/0276040 A1 11/2009 Rowe et al.
2009/0281619 A1 11/2009 Le et al.
2009/0299456 A1 12/2009 Melsheimer
2009/0319037 A1 12/2009 Rowe et al.
2010/0030318 A1 2/2010 Berra
2010/0036472 A1 2/2010 Papp
2010/0036473 A1 2/2010 Roth
2010/0049313 A1 2/2010 Alon et al.
2010/0076402 A1 3/2010 Mazzone et al.
2010/0076541 A1 3/2010 Kumoyama
2010/0082089 A1 4/2010 Quadri et al.
2010/0094394 A1 4/2010 Beach et al.
2010/0121425 A1 5/2010 Shimada
2010/0145431 A1 6/2010 Wu et al.
2010/0161036 A1 6/2010 Pintor et al.
2010/0174363 A1 7/2010 Castro

(56) References Cited

U.S. PATENT DOCUMENTS

2010/0198347 A1 8/2010 Zakay et al.
2010/0274344 A1 10/2010 Dusbabek et al.
2011/0015729 A1 1/2011 Jimenez et al.
2011/0054596 A1 3/2011 Taylor
2011/0137331 A1 6/2011 Walsh et al.
2011/0160846 A1 6/2011 Bishop et al.
2012/0123529 A1 5/2012 Levi et al.
2012/0239142 A1 9/2012 Liu et al.
2013/0030519 A1 1/2013 Tran et al.
2013/0123897 A1 * 5/2013 Robinson ................ A61F 2/966 623/1.11
2013/0190859 A1 * 7/2013 Hillukka ............... A61F 2/2418 623/2.11
2013/0317598 A1 11/2013 Rowe et al.
2014/0296962 A1 10/2014 Cartledge et al.
2016/0278955 A1 * 9/2016 Liu ........................... B65B 5/04
2017/0065415 A1 3/2017 Rupp et al.
2018/0153689 A1 6/2018 Maimon et al.
2018/0344456 A1 12/2018 Barash et al.
2018/0369004 A1 * 12/2018 Liu ........................... B65B 5/04
2020/0000589 A1 * 1/2020 Pasquino .............. A61F 2/2427
2020/0008941 A1 * 1/2020 Stappenbeck ............. A61F 2/95
2022/0039980 A1 * 2/2022 Stappenbeck ......... A61F 2/9525
2023/0061356 A1 * 3/2023 Goldberg .............. A61F 2/2436
2023/0301785 A1 * 9/2023 Robinson .............. A61F 2/9525

FOREIGN PATENT DOCUMENTS

EP 0592410 B1 10/1995
EP 0850607 A1 7/1998
FR 2815844 A1 5/2002
WO 1991017720 A1 11/1991
WO 1998029057 A1 7/1998
WO 1999012483 A1 3/1999
WO 2001049213 A2 7/2001
WO 2001054625 A1 8/2001
WO 2001076510 A2 10/2001
WO 2002022054 A1 3/2002
WO 2002036048 A1 5/2002
WO 2002047575 A2 6/2002
WO 2002060352 A1 8/2002
WO 2003030776 A2 4/2003
WO 2003047468 A1 6/2003
WO 2004019825 A1 3/2004
WO 2005084595 A1 9/2005
WO 2005102015 A2 11/2005
WO 2006032051 A2 3/2006
WO 2006111391 A1 10/2006
WO 2006138173 A2 12/2006
WO 2007047488 A2 4/2007
WO 2007067942 A1 6/2007
WO WO-2009035679 A1 * 3/2009 ............... A61F 2/86
WO 2010121076 A2 10/2010
WO WO-2015004173 A1 * 1/2015 ........... A61F 2/2436
WO WO-2022266003 A1 * 12/2022 ........... A61F 2/9525
WO WO-2025064644 A1 * 3/2025 ........... A61F 2/2412

* cited by examiner 308
360
300
306
310
328
354
302
342
160
322
316
320
358
372
348
350
168
304
146

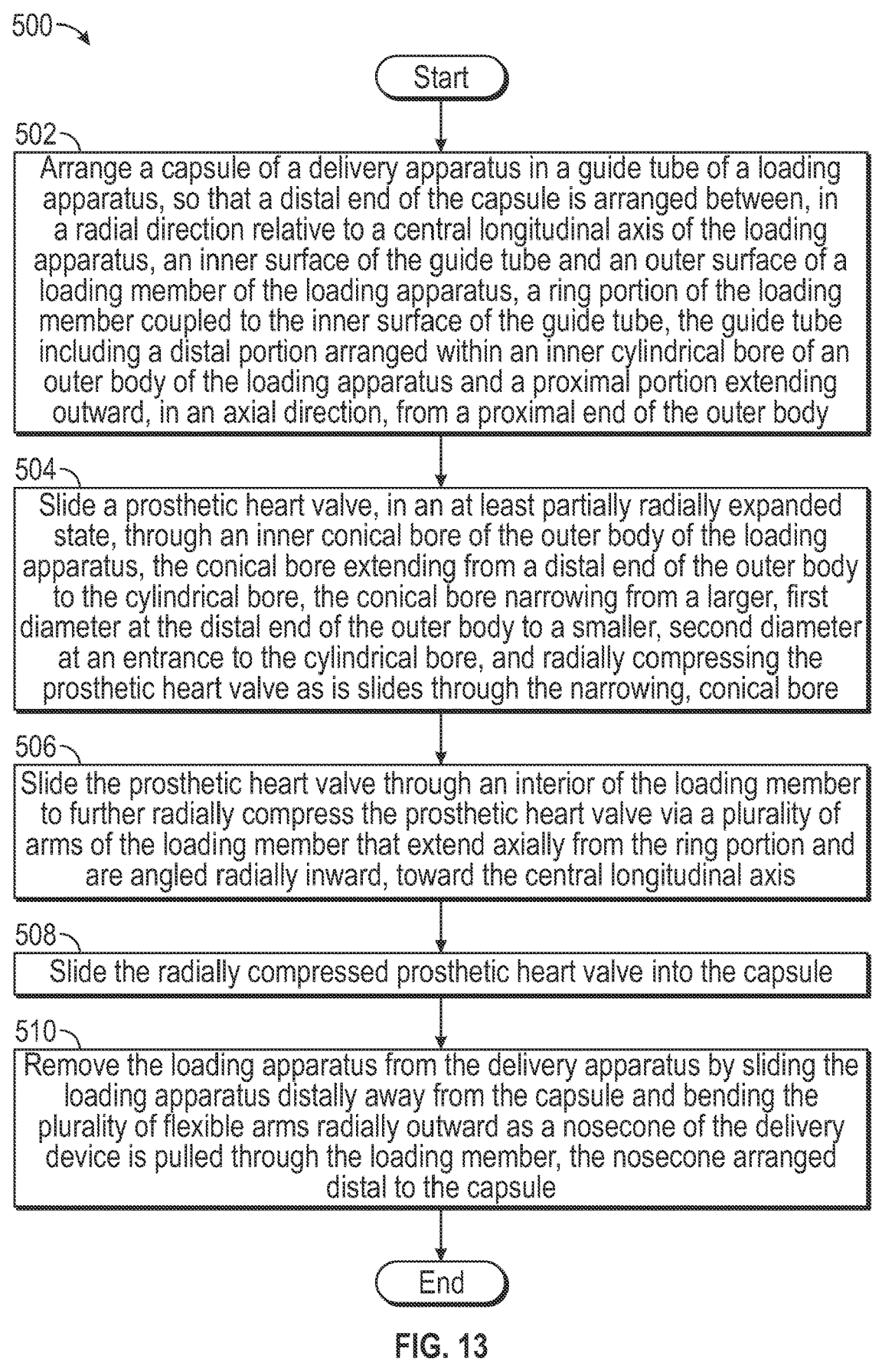

500

Start

502 Arrange a capsule of a delivery apparatus in a guide tube of a loading apparatus, so that a distal end of the capsule is arranged between, in a radial direction relative to a central longitudinal axis of the loading apparatus, an inner surface of the guide tube and an outer surface of a loading member of the loading apparatus, a ring portion of the loading member coupled to the inner surface of the guide tube, the guide tube including a distal portion arranged within an inner cylindrical bore of an outer body of the loading apparatus and a proximal portion extending outward, in an axial direction, from a proximal end of the outer body 504 Slide a prosthetic heart valve, in an at least partially radially expanded state, through an inner conical bore of the outer body of the loading apparatus, the conical bore extending from a distal end of the outer body to the cylindrical bore, the conical bore narrowing from a larger, first diameter at the distal end of the outer body to a smaller, second diameter at an entrance to the cylindrical bore, and radially compressing the prosthetic heart valve as is slides through the narrowing, conical bore 506 Slide the prosthetic heart valve through an interior of the loading member to further radially compress the prosthetic heart valve via a plurality of arms of the loading member that extend axially from the ring portion and are angled radially inward, toward the central longitudinal axis 508 Slide the radially compressed prosthetic heart valve into the capsule 510 Remove the loading apparatus from the delivery apparatus by sliding the loading apparatus distally away from the capsule and bending the plurality of flexible arms radially outward as a nosecone of the delivery device is pulled through the loading member, the nosecone arranged distal to the capsule End

FIG. 13

LOADING APPARATUS FOR LOADING A PROSTHETIC HEART VALVE INTO A DELIVERY APPARATUS

CROSS REFERENCE TO RELATED APPLICATION

This application is a continuation of PCT Patent Application No. PCT/US2021/028069, filed on Apr. 20, 2021, which application claims the benefit of U.S. Provisional Patent Application No. 63/013,146, filed Apr. 21, 2020, each of which application is incorporated herein in its entirety by this specific reference.

FIELD

The present disclosure concerns embodiments of a loading apparatus configured to load a prosthetic heart valve into a portion of a delivery apparatus.

BACKGROUND

The human heart can suffer from various valvular diseases. These valvular diseases can result in significant malfunctioning of the heart and ultimately require repair of the native valve or replacement of the native valve with an artificial valve. There are a number of known repair devices (e.g., stents) and artificial valves, as well as a number of known methods of implanting these devices and valves in humans. Percutaneous and minimally-invasive surgical approaches are used in various procedures to deliver prosthetic medical devices to locations inside the body that are not readily accessible by surgery or where access without surgery is desirable. In one specific example, a prosthetic heart valve can be mounted in a crimped state on the distal end of a delivery device, proximate to a nosecone of the delivery device, and advanced through the patient's vasculature (e.g., through a femoral artery and the aorta) until the prosthetic valve reaches the implantation site in the heart. The prosthetic valve is then expanded to its functional size, for example, by deploying the prosthetic valve from a capsule of the delivery device so that the prosthetic valve can self-expand or be expanded to its functional size.

In order to load the prosthetic valve into the capsule, a loading apparatus (e.g., loader) may be used. The loader can have an inner conical bore with a narrower, proximal edge that is arranged adjacent to the capsule. To load the prosthetic valve into the capsule, the prosthetic valve can be guided through the inner conical bore and into the capsule, the narrowing bore causing the prosthetic valve to be compressed down to a radially compressed configuration. The proximal edge of the conical bore can be provided with a diameter which is slightly narrower than an inner lumen of the capsule to facilitate easier loading. However, since the outer diameter of the nosecone, which is usually positioned distal to the capsule, is larger than the diameter of the narrowest diameter of the conical bore, removal of the loader after loading of the prosthetic valve may be prohibited by the nosecone. In some embodiments, the loader can be formed from separable portions that can be connected to each other during valve loading and detached from each other for releasing the loader. However, such loaders may be disadvantageous since undesired gaps may form between the separable portions.

Accordingly, improvements in a valve loader or loading apparatus which allows for loading of a prosthetic valve into a capsule of a delivery apparatus that includes a nosecone and removal of the loader from the delivery apparatus after loading is complete, are desirable.

SUMMARY

Disclosed herein are embodiments of a loading apparatus (e.g., loader) for loading a prosthetic heart valve into a capsule of a delivery apparatus, as well as related methods for use of such a loading apparatus. The loading apparatus can be configured (e.g., shaped) to compress an expanded, prosthetic heart valve down into a compressed configuration and load it into the capsule of the delivery apparatus in this compressed configuration. The loading apparatus can be further configured to enable removal of the delivery apparatus from the loading apparatus via sliding a nosecone of the delivery apparatus through an interior of the loading apparatus, in a same direction as the prosthetic heart valve is loaded into the capsule.

In one representative embodiment, a loading apparatus includes: an outer body including an inner conical bore that narrows in diameter from a distal end to a proximal end portion of the outer body; a guide tube including a distal portion arranged within the proximal end portion of the outer body and a proximal portion extending outward from the outer body; and an annular loading member including a ring portion and a plurality of arms extending outward, in an axial direction relative to a central longitudinal axis of the loading apparatus, from the ring portion. The plurality of arms is arranged around a circumference of the ring portion and the ring portion is coupled to an inner surface of the distal portion of the guide tube.

In another representative embodiment, a method for loading a prosthetic heart valve into a capsule of a delivery apparatus includes arranging the capsule of the delivery apparatus in a guide tube of a loading apparatus, so that a distal end of the capsule is arranged between, in a radial direction relative to a central longitudinal axis of the loading apparatus, an inner surface of the guide tube and an outer surface of a loading member of the loading apparatus, a ring portion of the loading member coupled to the inner surface of the guide tube, the guide tube including a distal portion arranged within an inner cylindrical bore of an outer body of the loading apparatus and a proximal portion extending outward, in an axial direction, from a proximal end of the outer body. The method further includes radially compressing the prosthetic heart valve by sliding the prosthetic heart valve through an inner conical bore of the outer body of the loading apparatus, the conical bore narrowing from a distal end of the outer body to the cylindrical bore, and by sliding the prosthetic heart valve through a plurality of arms of the loading member that extend axially outward from the ring portion and angle radially inward toward the central longitudinal axis. The method further includes sliding the radially compressed prosthetic heart valve from the loading member into the capsule to load the prosthetic heart valve into the capsule. The method further includes removing the loading apparatus from the delivery apparatus by sliding the loading apparatus distally away from the capsule and bending the plurality of arms radially outward as a nosecone of the delivery device is pulled through the loading member, the nosecone arranged distal to the capsule.

In another representative embodiment, a method for loading a prosthetic heart valve into a capsule of a delivery apparatus includes arranging the capsule of the delivery apparatus in a guide tube of a loading apparatus, so that a distal end of the capsule is arranged between, in a radial direction relative to a central longitudinal axis of the loading apparatus, an inner surface of the guide tube and an outer surface of an annular loading member of the loading apparatus, a ring portion of the loading member coupled to the inner surface of the guide tube, the guide tube including a distal portion arranged within an inner cylindrical bore of an outer body of the loading apparatus and a proximal portion extending outward, in an axial direction, from a proximal end of the outer body. The method further includes sliding a prosthetic heart valve, in an at least partially radially expanded state, through an inner conical bore of the outer body of the loading apparatus, the conical bore extending from a distal end of the outer body to the cylindrical bore, the conical bore narrowing from a larger, first diameter at the distal end of the outer body to a smaller, second diameter at an entrance to the cylindrical bore, and radially compressing the prosthetic heart valve as is slides through the narrowing, conical bore. The method further includes sliding the prosthetic heart valve through an interior of the loading member to further radially compress the prosthetic heart valve via a plurality of flexible arms of the loading member that extend axially from the ring portion and are angled radially inward, toward the central longitudinal axis, the plurality of flexible arms arranged around a circumference of the ring portion, wherein proximal ends of the plurality of flexible arms are spaced away from one another around a circumference of the loading member and are configured to flex in a radial direction relative to the central longitudinal axis. The method further includes sliding the radially compressed prosthetic heart valve into the capsule.

In another representative embodiment, a loading apparatus includes: an outer body including an inner conical bore and an inner cylindrical bore that are continuous with one another along a length of the outer body, the conical bore narrowing in diameter from a distal end of the outer body to the cylindrical bore and the cylindrical bore extending from a narrowed end of the conical bore to a proximal end of the outer body; a guide tube including a distal portion arranged within the cylindrical bore and a proximal portion extending outward from the proximal end of the outer body; and an annular loading member including a ring portion and a plurality of flexible arms arranged around a circumference of the loading member, the plurality of flexible arms extending outward, in an axial direction relative to a central longitudinal axis of the loading apparatus, from the ring portion, the ring portion coupled to an inner surface of the distal portion of the guide tube, and wherein proximal ends of the plurality of flexible arms, arranged away from the ring portion, are angled radially inward toward the central longitudinal axis when the annular loading member is in a loading, first configuration.

The foregoing and other objects, features, and advantages of the disclosed technology will become more apparent from the following detailed description, which proceeds with reference to the accompanying figures.

BRIEF DESCRIPTION OF THE DRAWINGS

FIG. 13 is a flow chart of an exemplary method for loading a prosthetic heart valve into a capsule of a delivery apparatus using a loading apparatus.

DETAILED DESCRIPTION

General Considerations

Figure 1:
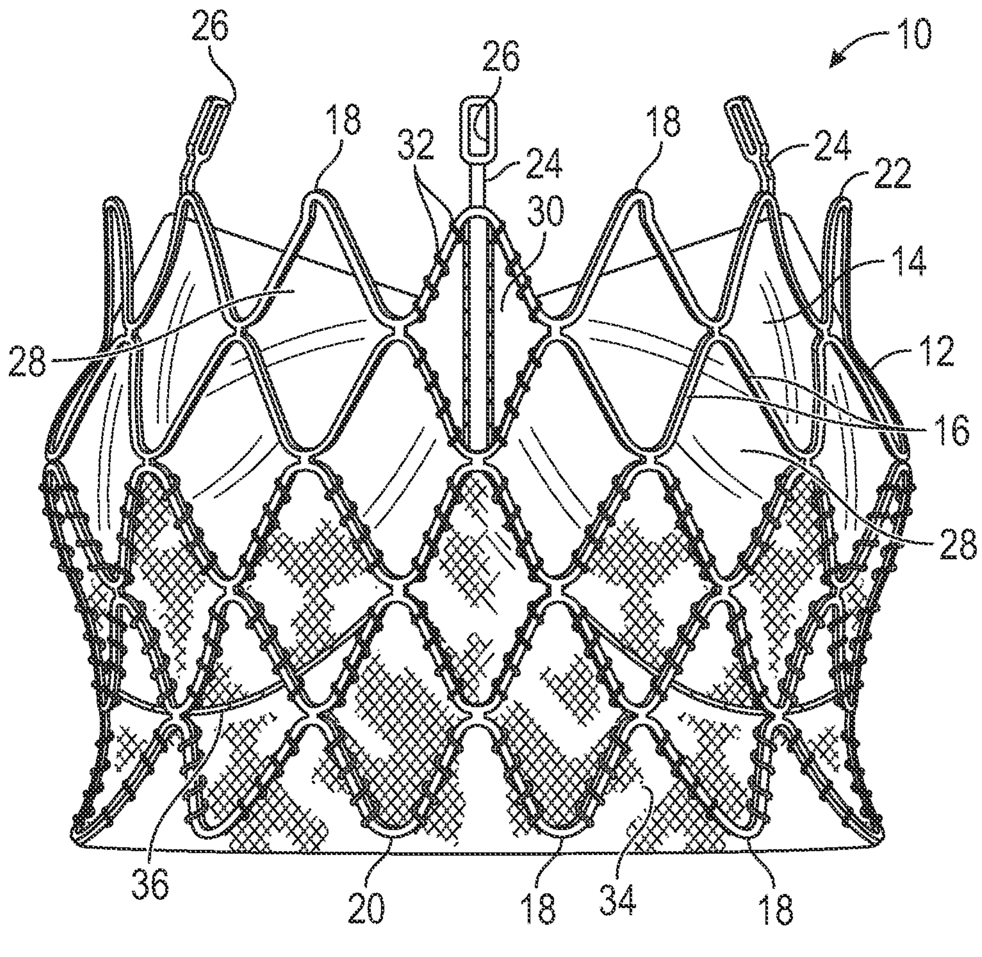
FIG. 1 is a side elevation view of an exemplary embodiment of an implantable prosthetic heart valve that can be loaded into a capsule of a delivery apparatus using a loading apparatus, as disclosed herein.

For purposes of this description, certain aspects, advantages, and novel features of the embodiments of this disclosure are described herein. The described methods, systems, and apparatus should not be construed as limiting in any way. Instead, the present disclosure is directed toward all novel and non-obvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present, or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a," "an," and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C," or "A, B, and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and "or."

As used herein, with reference to the prosthetic heart valve, the delivery apparatus, and the loading apparatus, "proximal" refers to a position, direction, or portion of a component that is closer to the user and/or a handle of the delivery apparatus that is outside the patient, while "distal" refers to a position, direction, or portion of a component that is further away from the user and/or the handle of the delivery apparatus and closer to the implantation site. The terms "longitudinal" and "axial" refer to an axis extending in the proximal and distal directions, unless otherwise expressly defined. Further, the term "radial" refers to a direction that is arranged perpendicular to the axis and points along a radius from a center of an object (where the axis is positioned at the center, such as the longitudinal axis of the prosthetic valve).

Examples of the Disclosed Technology

Described herein are examples of a loading apparatus that can be used to compress a prosthetic heart valve and load the prosthetic heart valve, in a radially compressed configuration, into a capsule of a delivery apparatus. The disclosed loading apparatus can include an outer body including an inner conical bore that narrows from a distal end to a proximal end portion of the outer body. The loading apparatus can further include a guide tube including a distal portion arranged within the proximal end portion of the outer body and a proximal portion extending outward from the outer body. The loading apparatus can further include an annular loading member including a ring portion and a plurality of arms extending outward, in an axial direction relative to a central longitudinal axis of the loading apparatus, from the ring portion, the ring portion coupled to an inner surface of the distal portion of the guide tube.

In some embodiments, the delivery apparatus is configured to deliver and implant the prosthetic heart valve, such as the example prosthetic heart valve of FIG. 1, at a selected implantation site within a patient (e.g., within the native aortic valve, mitral valve, tricuspid valve or pulmonary valve). For example, by retracting the capsule of the delivery apparatus away from the radially compressed prosthetic heart valve, the prosthetic heart valve can expand to is expanded configuration and implant itself at the target implantation site.

Figure 2:
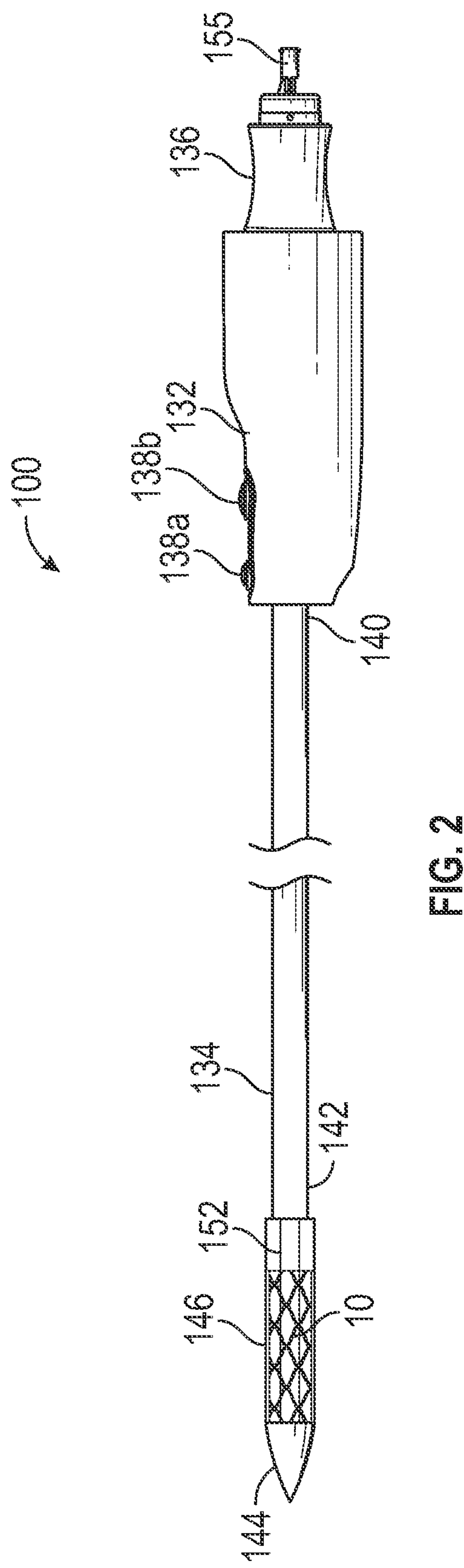
FIG. 2 is a cross-sectional side view of an exemplary embodiment of a delivery apparatus for delivering the prosthetic heart valve of FIG. 1 to a target implantation site, the delivery apparatus including a capsule for retaining the prosthetic heart valve therein in a compressed configuration.

FIG. 1 shows a prosthetic heart valve 10, according to one embodiment, that can be implanted with a delivery apparatus 100 of FIG. 2. In some embodiments, the prosthetic heart valve 10 is a self-expanding valve that is delivered in a radially compressed state to a deployment site via the delivery apparatus 100. When advanced from a delivery capsule at the distal end of the delivery apparatus (FIG. 2), the prosthetic valve can radially self-expand to its functional size.

The prosthetic heart valve 10 comprises a stent, or frame 12 and a valvular structure 14 (e.g., leaflets or a flap valve) supported by the frame 12. The frame 12 can have a plurality of interconnected struts 16 arranged in a lattice-like pattern and forming a plurality of apices 18 at the inflow and outflow ends 20, 22, respectively, of the frame 12

The frame 12 can include a plurality of angularly-spaced posts 24 extending from respective apices 18 at the outflow end of the frame 12. The frame 12 in the illustrated embodiment includes three such posts 24, although a greater or fewer number of posts can be used. In one implementation, the frame 12 can have posts extending from all the apices 18 at the outflow end of the frame. Each post 24 can have an eyelet or aperture 26, which can be used to form a releasable connection with the delivery apparatus 100.

In some embodiments, the frame 12 can be without posts 24 and apertures 26 can be formed in the apices 18 at the outflow end of the frame.

In other embodiments, the apertures 26 (whether formed in posts 24 or in the apices 18) can be formed at the inlet (or inflow) end 20 of the frame 12 where other delivery apparatus configurations or other delivery techniques require apertures at the inlet end of the frame, such as a transapical delivery approach.

In particular embodiments, the prosthetic heart valve 10 is a self-expandable heart valve wherein the frame 12 is a made of a super-elastic, self-expanding material (e.g., a nickel titanium alloy such as Nitinol), as is known in the art. When used with the delivery apparatus 100 (FIG. 2), the prosthetic valve 10 can self-expand from a radially compressed state to a radially expanded state when advanced from a delivery capsule (e.g., a delivery sheath) of the delivery apparatus.

In other embodiments, the frame 12 can be made of any of various suitable plastically-expandable materials (e.g., stainless steel, cobalt-chromium alloy, etc.) and the prosthetic heart valve can be expanded from a radially compressed state to a radially expanded state by actuating other expansion means of the delivery apparatus that produces radial expansion of the prosthetic valve.

The valvular structure 14 can comprise a plurality of leaflets 28. The valvular structure typically comprises three leaflets 28 arranged in a tricuspid arrangement, although a greater or fewer number of leaflets 28 can be used. The leaflets 28 can be made of any various suitable materials, including natural tissue (e.g., bovine pericardium or pericardium from other sources) or synthetic materials (e.g., polyurethane). Adjacent side portions at the outflow edges (the upper edges in the drawings) of adjacent leaflets can be secured to each other to form commissures 30 of the valvular structure, which can be secured to the frame with sutures 32.

The prosthetic valve 10 can further include an inner skirt 34 mounted on the inside of the frame 12. The skirt 34 helps establish a seal with the surrounding tissue after implantation. The skirt 34 can also be used to mount portions of the leaflets 28 to the frame 12. For example, in the illustrated embodiment, the inflow edges of the leaflets (the lower edges in the drawings) can be sutured to the skirt 34 along suture line 36. The skirt 34 can be connected directly to the frame 12, such as with sutures. Although not shown, the prosthetic valve 10 can include an outer skirt mounted on the outside of the frame in lieu of or in addition to the inner skirt 34 to further seal the prosthetic valve against surrounding tissue. The inner and/or outer skirts can be made of any of various suitable materials, including natural tissue (e.g., pericardium tissue) or any of various synthetic materials, which may be woven, non-woven, braided, knitted, and/or combinations thereof. In one specific implementation, the inner skirt 34 is made of a polyethylene terephthalate (PET) fabric.

Exemplary configurations of the prosthetic heart valve are further disclosed in U.S. Pat. Nos. 9,867,700, 9,393,110, 7,993,394, and 8,652,202, the disclosures of which are incorporated herein by reference.

Figure 3:
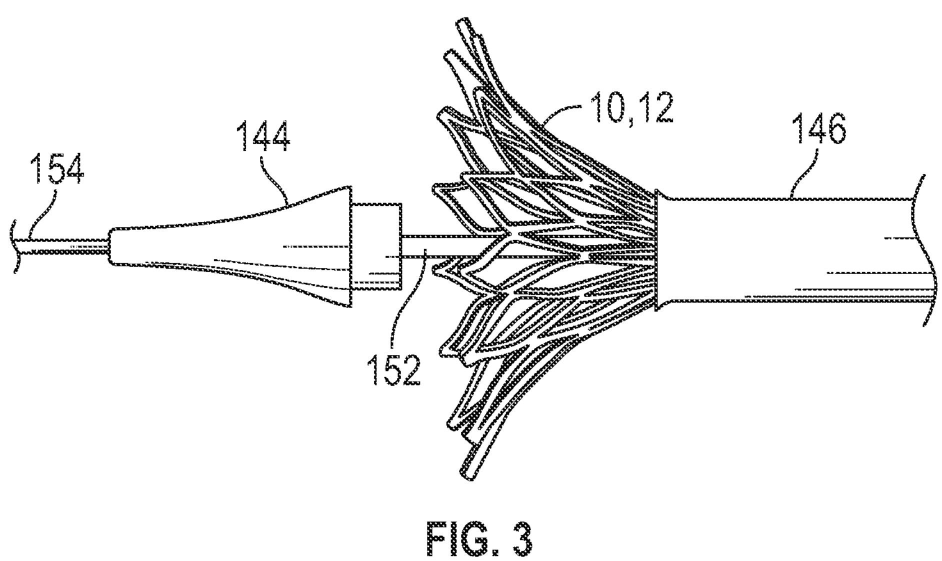
FIG. 3 is a side elevation view of the distal end portion of the delivery apparatus of FIG. 2 shown with the capsule of the delivery apparatus advanced over a portion of the prosthetic heart valve frame.

Prosthetic heart valve 10, or another type of implantable, expandable medical device, such as an expandable stent, can be delivered to an implantation site via delivery apparatus 100, an embodiment of which is shown at FIGS. 2 and 3.

In an exemplary embodiment shown in FIG. 2, the delivery apparatus 100 can comprise a handle portion 132 and a first shaft 134 extending distally therefrom. A user, such as a physician or clinician, can operate the delivery apparatus 100 via actuation of a plurality of knobs 136, dials, and/or buttons 138*a*, 138*b* located on the handle portion 132. The first shaft 134 has a proximal end portion 140 and a distal end portion 142. The proximal end portion 140 of the first shaft 134 can be coupled to the handle portion 132.

As shown in FIG. 2, the delivery apparatus 100 can include a second shaft 152. The second shaft 152 extends distally from the handle portion 132 and co-axially though the first shaft 134. In the illustrated embodiment, the first shaft 134 is the outermost shaft of the delivery apparatus and therefore can be referred to as the outer shaft 134 of the delivery apparatus. In the illustrated embodiment, the second shaft 152 is the innermost shaft of the delivery apparatus and therefore can be referred to as the inner shaft 152 of the delivery apparatus. In some embodiments, the delivery apparatus 100 may include a third shaft that is an intermediate shaft, arranged between the inner 152 shaft and the outer shaft 134.

A nosecone 144 can be connected to or mounted on a distal end portion of the inner shaft 152. The nosecone 144 can have a tapered outer surface as shown for atraumatic tracking of the delivery apparatus 100 through a patient's vasculature. The inner shaft 152 extends through the prosthetic valve 10.

In certain embodiments, the first and second shafts 134 and 152, respectively, can be configured to be moveable relative to each other, including relative axial movement (in the proximal and distal directions) and/or relative rotational movement (in the clockwise and counterclockwise directions). A guide wire 154 (as shown in FIG. 3) can extend through the central lumen of the inner shaft 152 and the inner lumen of the nosecone 144 so that the delivery apparatus 100 can be advanced over the guide wire 154 inside the patient's vasculature during delivery of the prosthetic valve 10. The guide wire 154 may be inserted into the inner shaft 152 via a proximal port 155 of the handle portion 132 (FIG. 2).

A delivery capsule 146 is coupled to the distal end portion 142 of the first shaft 134, proximal to the nosecone 144. The delivery capsule 146 houses the prosthetic valve 10 therein, in a radially compressed state, as shown at FIGS. 2-3. In one embodiment, the delivery capsule 146 covers and retains the underlying compressed prosthetic valve of FIG. 1. The delivery apparatus 100 is particularly suited for delivering and implanting a self-expandable prosthetic valve 10 that radially expands to its functional size under its own resiliency when deployed from the delivery capsule 146.

As shown at FIG. 2, the delivery capsule 146 is configured to accommodate the prosthetic heart valve 10, or another type of prosthetic heart valve or implantable medical device, in a radially compressed state for delivery into a patient's vasculature. FIG. 3 shows the delivery capsule 146 advanced over a portion of the prosthetic heart valve 10.

In some embodiments, a valve-retaining mechanism can be used to form a releasable connection between the prosthetic valve 10 and the delivery apparatus 100. For example, in some embodiments, the posts 24 of the frame 12 can be retained in corresponding recesses of a shaft or retaining member of the delivery apparatus, which allow the posts of the frame to expand out of their corresponding recesses when the capsule 146 is retracted to deploy the prosthetic valve (e.g., see retaining member 406 in FIG. 11, as described further below). In other embodiments, the retaining mechanism can comprise inner and outer metal fork members that form a release connection between the delivery apparatus and the prosthetic valve. Further details regarding the delivery apparatus, including alternative valve-retaining mechanisms, are disclosed in U.S. Pat. Nos. 9,867,700, 9,155,619 and 8,652,202, the disclosures of which are incorporated herein by reference.

Figure 4:
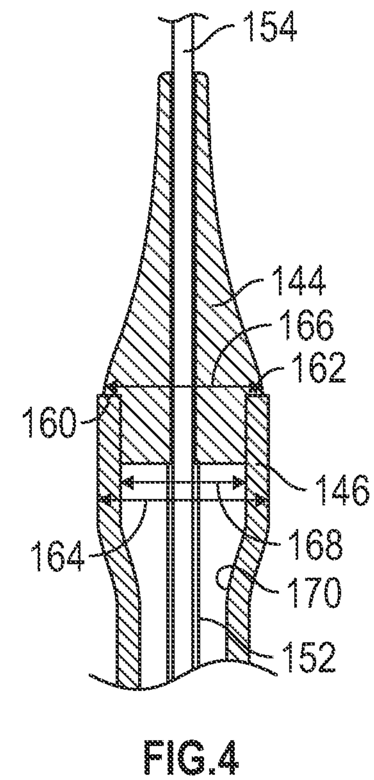
FIG. 4 is a cross-sectional side view of a portion of a distal end portion of a delivery apparatus illustrating an arrangement of a capsule relative to a nosecone of the delivery apparatus.

As shown in FIG. 4, in a delivery configuration of the delivery apparatus 100 (e.g., a configuration in which the delivery apparatus is advanced through a patient's vasculature to a target implantation site for the prosthetic valve 10), the capsule 146 is arranged adjacent to the nosecone 144. For example, a distal edge 160 of the capsule 146 abuts a proximal shoulder 162 of the nosecone 144.

In order to form a relatively smooth transition between the capsule 146 and the nosecone 144, an outer diameter 164 of the capsule 146 can closely match an outer diameter 166 of the nosecone 144. An inner diameter 168 of an inner lumen 170 the capsule 146, which is adapted to receive a prosthetic heart valve therein in its radially compressed state, is narrower than the outer diameter 166 of the nosecone 144.

To deploy the prosthetic valve 10 from the capsule 146, the shaft 134 can be retracted proximally relative to the prosthetic valve and the inner shaft 152. The shaft 134 in turn retracts the capsule 146 and allows the prosthetic valve 10 to self-expand to its functional size at a deployment site (as shown at FIG. 3). Prior to or at the same time as retracting the capsule, the nosecone 144 can be advanced distally relative to the capsule by advancing the inner shaft 152 in the distal direction. In other embodiments, such as disclosed in U.S. Pat. Nos. 9,867,700, 9,155,619 and 8,652,202, the delivery apparatus 100 can have an inner torque shaft (not shown) extending through the shaft 134, wherein rotation of the torque shaft is effective to retract the capsule 146 relative to the shaft 134 and the prosthetic valve to deploy the prosthetic valve from the capsule.

Figure 5:
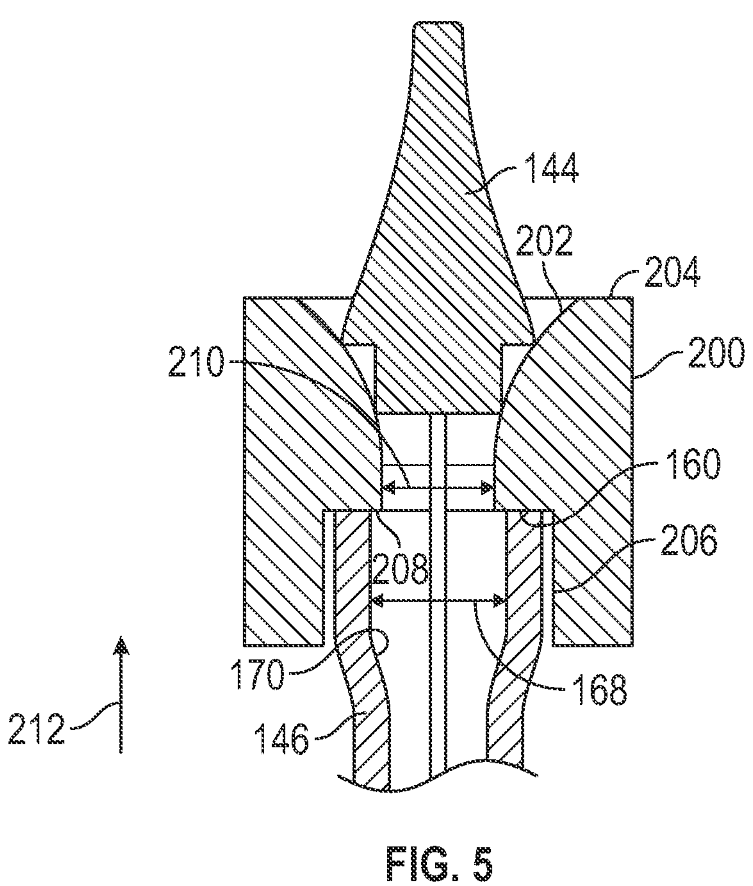
FIG. 5 is a cross-sectional side view of a conventional valve loading apparatus positioned against a distal end of an exemplary capsule of a delivery apparatus.

FIG. 5 shows an embodiment of a valve loading apparatus (referred to herein as a loader) 200 which can be used to load a prosthetic heart valve into an inner lumen of a capsule of a delivery apparatus, such as capsule 146 of delivery apparatus 100 (as shown in FIGS. 2-4).

As shown in FIG. 5, the loader 200 includes an internal conical bore 202 that narrows from a distal end 204 of the loader 200 to an inner, receiving portion 206 of the loader that is adapted to receive the capsule 146 (or another capsule of another delivery apparatus) therein. For example, an interior edge 208 of the receiving portion 206 abuts the distal edge 160 of the capsule 146.

Thus, an at least partially radially expanded prosthetic heart valve (not shown in FIG. 5) can be slid through the conical bore 202 and into the inner lumen 170 of the capsule 146.

In some embodiments, the narrowest, inner diameter 210 of the conical bore 202, which is arranged at the conical bore's proximal end, proximate to the receiving portion 206 of the loader 200, can be narrower than the inner diameter 168 of the capsule 146, in order to enable easier valve loading into the capsule 146.

When the valve is fully loaded in the capsule 146, the loader 200 should be removed by sliding it in a distal direction 212, away from the capsule 146 and a remainder of the delivery apparatus. However, as shown in FIGS. 4 and 5, the delivery apparatus includes the nosecone 144, positioned distally to the capsule 146. Since the narrowest, inner diameter 210 of the loader 200 is narrower than the outer diameter 166 of the nosecone 144, the nosecone 144 will prevent removal of the loader 200 when moved distally from the capsule 146.

In some embodiments, a loader comprised of two separable components may be removed from a delivery apparatus by detaching the two separable components from each other. However, there may be issues with such a loader, such as irregularities that may form between the two separable components.

Thus, a valve loader (e.g., loading apparatus) which allows for loading of a prosthetic valve into a capsule of a delivery apparatus that includes a nosecone and that is configured to be easily removed from the delivery apparatus after loading is complete without disassembly of the loader, is desired.

Figure 6:
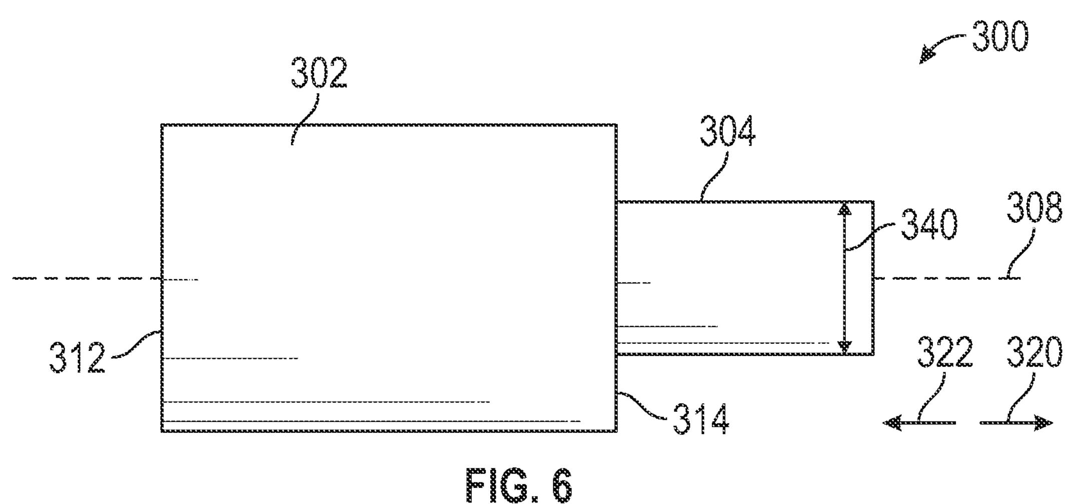
FIG. 6 is a side elevation view of an exemplary loading apparatus configured to load a prosthetic heart valve into a capsule of a delivery apparatus including a distally arranged nosecone.
Figure 7:
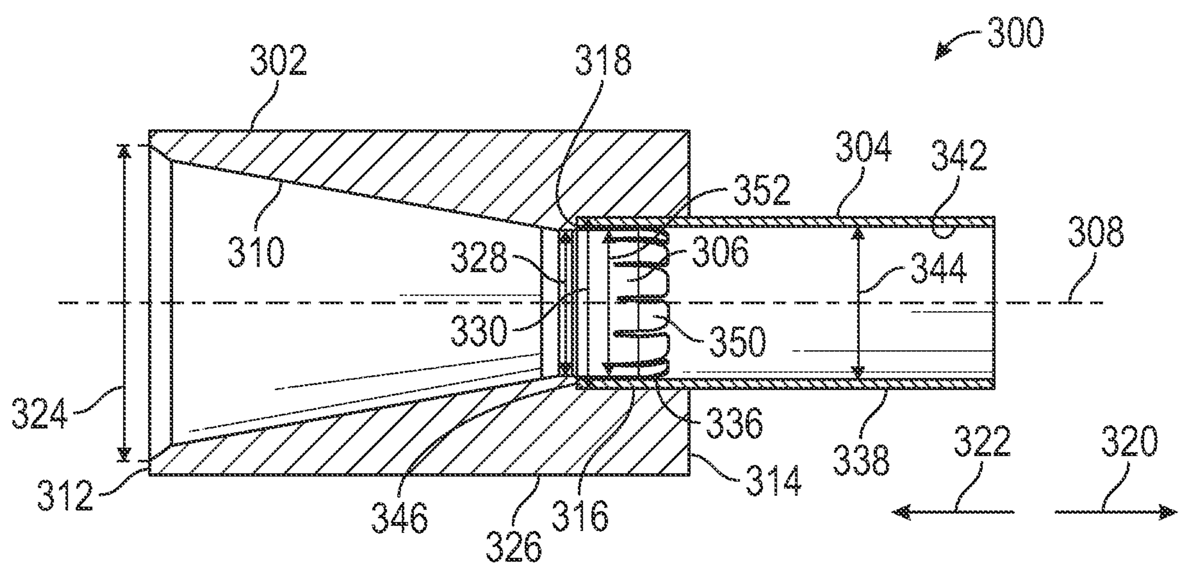
FIG. 7 is a cross-sectional side view of the loading apparatus of FIG. 6.
Figure 8:
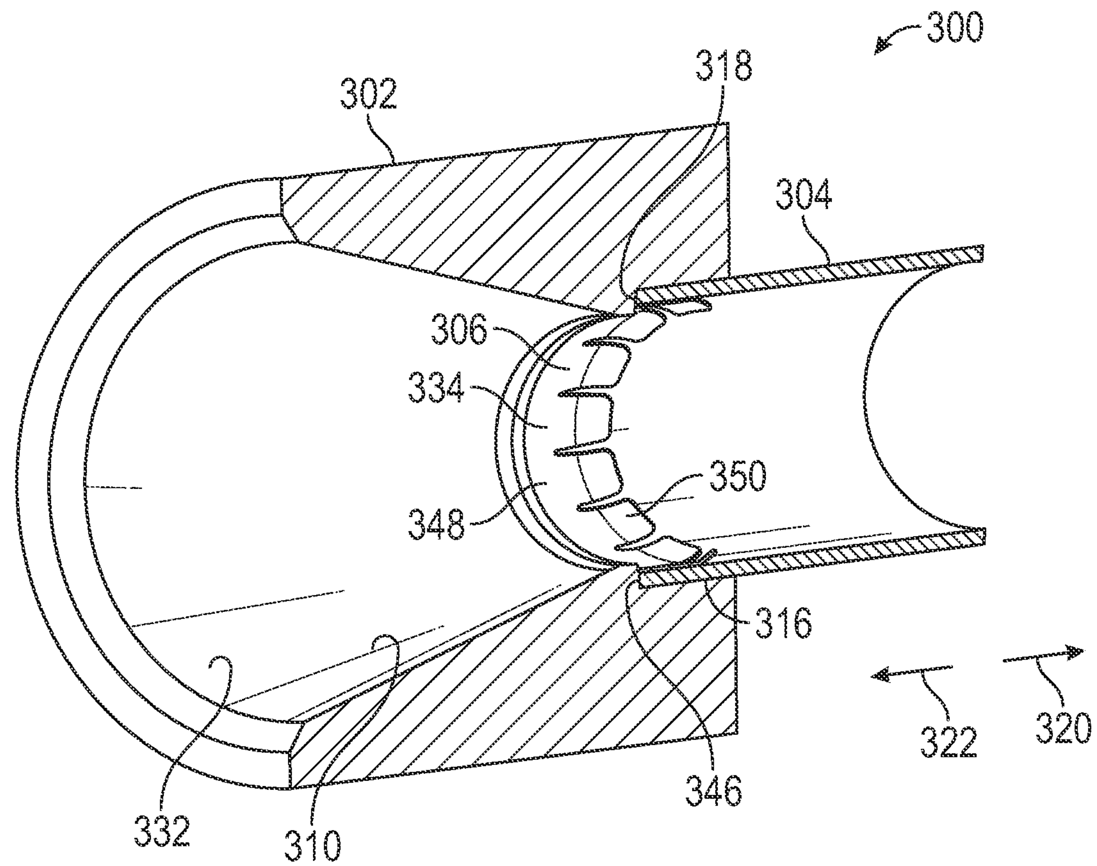
FIG. 8 is a cross-sectional perspective view of the loading apparatus of FIG. 6.
Figures 9, 10:
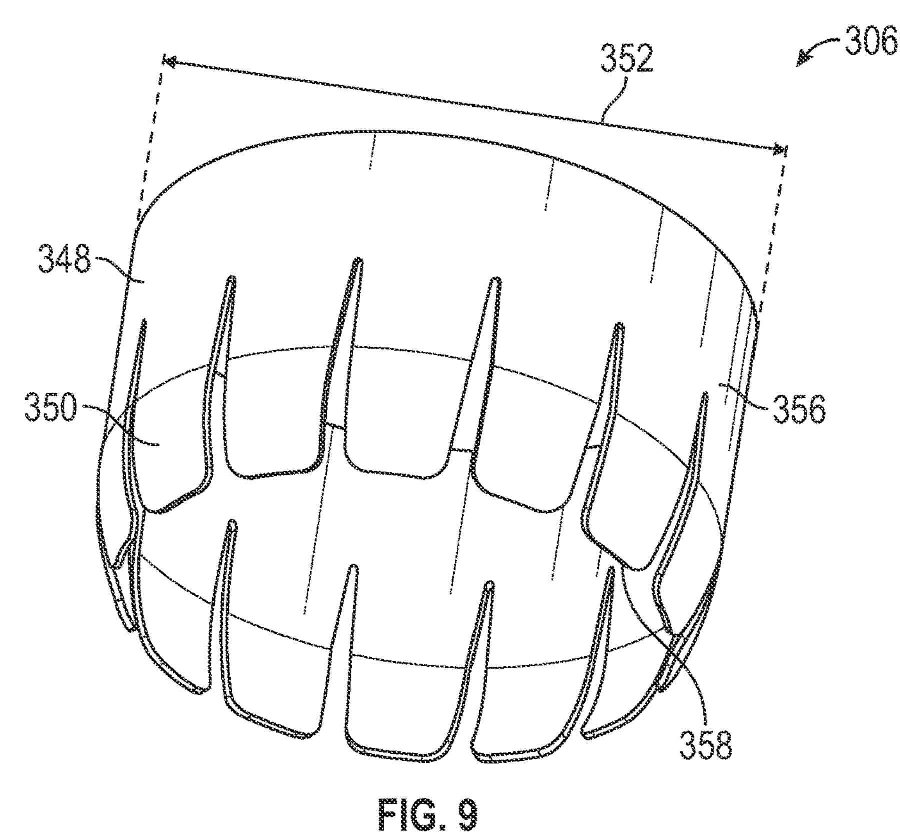
FIG. 9 is a perspective view of an annular loading member of the loading apparatus of FIG. 6.
FIG. 10 is a cross-sectional side view of a capsule of a delivery apparatus arranged within the loading apparatus of FIG. 6.

FIGS. 6-9 show an embodiment of a loading apparatus (e.g., loader) 300 that is configured to load a prosthetic heart valve into a capsule of a delivery apparatus and be removed from the delivery apparatus, after valve loading is complete. FIGS. 6, 7, and 8 show a side view, sectional side view, and sectional perspective view, respectively, of the loader 300, in an assembled configuration. FIG. 9 shows a perspective view of an annular loading member of the loader 300 (disassembled from a remainder of the loader 300).

As shown in FIGS. 6-8, the loader 300 includes an outer body 302, a guide tube 304, and an annular loading member 306 (FIGS. 7 and 8). The loader 300 has a central longitudinal axis 308 arranged along a length of the loader 300. FIGS. 6-8 shows a proximal direction 320 and distal direction 322, arranged in parallel with the central longitudinal axis 308, for reference. The guide tube 304 extends in the proximal direction 320, outward and away from a proximal end 314 of the outer body 302.

The outer body 302 includes an inner conical bore 310 and an inner cylindrical bore 316 (shown in FIGS. 7 and 8) that are arranged adjacent to and are continuous with one another to form a continuous inner surface of the outer body 302 that extends from a distal end 312 to the proximal end 314 of the outer body 302. The conical bore 310 narrows in diameter from the distal end 312 to a transition (e.g., transition region) 318 between the conical bore 310 and the cylindrical bore 316 (which, in some embodiments, may include a step transition or, in other embodiments, may include an angled transition). For example, the conical bore 310 can include a widened end having a wider, first diameter 324 and a narrowed end, arranged within a proximal end portion 326 of the outer body 302, having a narrower, second diameter 328 (shown in FIG. 7). Thus, in some embodiments, the conical bore 310 may have a funnel shape.

In some embodiments, the cross-section of the conical bore 310 can be circular, having the first diameter 324 and the second diameter 328.

In alternate embodiments, the cross-section of the conical bore 310 can be elliptical, with a major axis (larger diameter) and a minor axis (smaller diameter). Thus, in some embodiments, the first diameter 324 may be the minor axis of the elliptical cross-section at the widened end and the second diameter 328 may be the minor axis of the elliptical cross-section at the narrowed end.

In some embodiments, as shown in FIG. 7, the cylindrical bore 316 can have a third diameter 330 that is slightly larger than the second diameter 328 of the narrowed end of the conical bore 310 and smaller than the first diameter 324 of the widened end of the conical bore 310. In some embodiments, as shown in FIG. 7, a difference between the third diameter 330 and the second diameter 328 can provide space to accommodate a thickness of the guide tube 304 and the loading member 306. In this way, a continuous inner surface can be provided by and between an inner surface 332 of the conical bore 310 and an inner surface 334 of the loading member 306 (shown in FIG. 8).

As shown in FIG. 7, the guide tube 304 includes a distal portion 336 arranged within the cylindrical bore 316 and a proximal portion 338 that extends outward and away from the proximal end 314 of the outer body 302, in the proximal direction 320. In some embodiments, the guide tube 304 has an outer diameter 340 (shown in FIG. 6) that may be approximately the same as the third diameter 330 of the cylindrical bore and an inner surface 342 of the guide tube 304 that has an inner diameter 344 (shown in FIG. 7). In other embodiments, the outer diameter 340 can be slightly smaller than the third diameter 330 in order to allow the distal portion 336 of the guide tube 304 to fit within the cylindrical bore 316.

In some embodiments, the guide tube 304 can comprise a relatively rigid material, such as a relatively rigid metal (e.g., stainless steel) or a rigid polymer. In some embodiments, the guide tube 304 can be press fit within the cylindrical bore 316 (such that it is coupled to and within the cylindrical bore 316). In alternate embodiments, the guide tube 304 can be secured to and within the cylindrical bore 316 of the outer body 302 via welding, an adhesive, or another fastening means.

In some embodiments, the outer body 302 can comprise a relatively rigid metal or polymeric (plastic) material.

As shown in FIGS. 7 and 8, a distal end 346 of the guide tube 304 abuts (and has face-sharing contact with) an edge of the transition 318 between the conical bore 310 and the cylindrical bore 316.

The annular loading member 306 (shown by itself in FIG. 9) includes a ring portion 348 and a plurality of arms (e.g., extensions) 350 that extend outward from the ring portion 348, in the axial direction. The ring portion 348 is annular and has an outer diameter 352. In some embodiments, an inner diameter 354 of the ring portion 348 (shown in FIG. 10) can be approximately the same as the second diameter 328. In other embodiments, the inner diameter of the loading member may be slightly larger than the second diameter 328.

As shown in FIG. 9, each of the arms 350 extends outward, in the proximal direction (e.g., proximally along the axial direction) 320 from the ring portion 348. Further, each of the arms 350 can include a wider, distal end 356 arranged at (e.g., attached or coupled to and continuous with) the ring portion 348 and a narrower, proximal end 358 that is arranged away from the ring portion 348. For example, each distal end 356 is wider, in a circumferential direction, than the corresponding proximal end 358. In this way, each arm 350 tapers in width, from its distal end 356 to its proximal end 358.

Each proximal end 358 of each arm 350 is spaced away from the proximal ends 358 of adjacent arms 350. In this way, the proximal ends 358 of the plurality of arms 350 are spaced apart from one another around a circumference of the loading member 306.

In some embodiments, each arm 350 can be connected to the ring portion, not only at its distal end 356, but at another portion of the arm, such as at a middle portion of the arm 350. For example, in some embodiments, additional material may connect a middle portion of each arm 350 to a remainder (e.g., the ring portion 348) of the loading member 306.

In some embodiments, an inner surface and/or outer surface of one or more of the plurality of arms 350 can be individually coated with a low friction coating (e.g., Teflon). In other embodiments, all the plurality of arms 350 can be laminated (or coated) with a continuous layer (e.g., cylindrical layer) of a low friction coating or hard coating (e.g., ceramic, TiN, CVD, or diamond) on an inner side and/or outer side of the loading member 306. In other embodiments, as described further below with reference to FIG. 14, the inner surface 334 of the arms 350 and/or the entire loading member 306 can have a surface roughness, configured as a plurality of small protrusions or depressions (pits or dimples), that are configured to reduce frictional forces between the inner surface 334 and a component sliding through the loading member 306. In this way, components moving through an interior of the loading member 306 (e.g., the prosthetic valve or the nosecone) may slide more easily through the arms 350.

In some embodiments, the plurality of arms 350 are flexible arms, where each flexible arm 350 is configured to flex (e.g., bend) radially inward and/or outward, relative to the central longitudinal axis 308. In some embodiments, the flexible arms 350 can comprise an elastically deformable material, such as an elastically deformable metal or polymeric material. For example, in some embodiments, the flexible arms 350 and/or the entire loading member 306 can comprise a relatively thin plastic or metal material, where the proximal ends 358 are configured to flex or bend under pressure.

Figure 11:
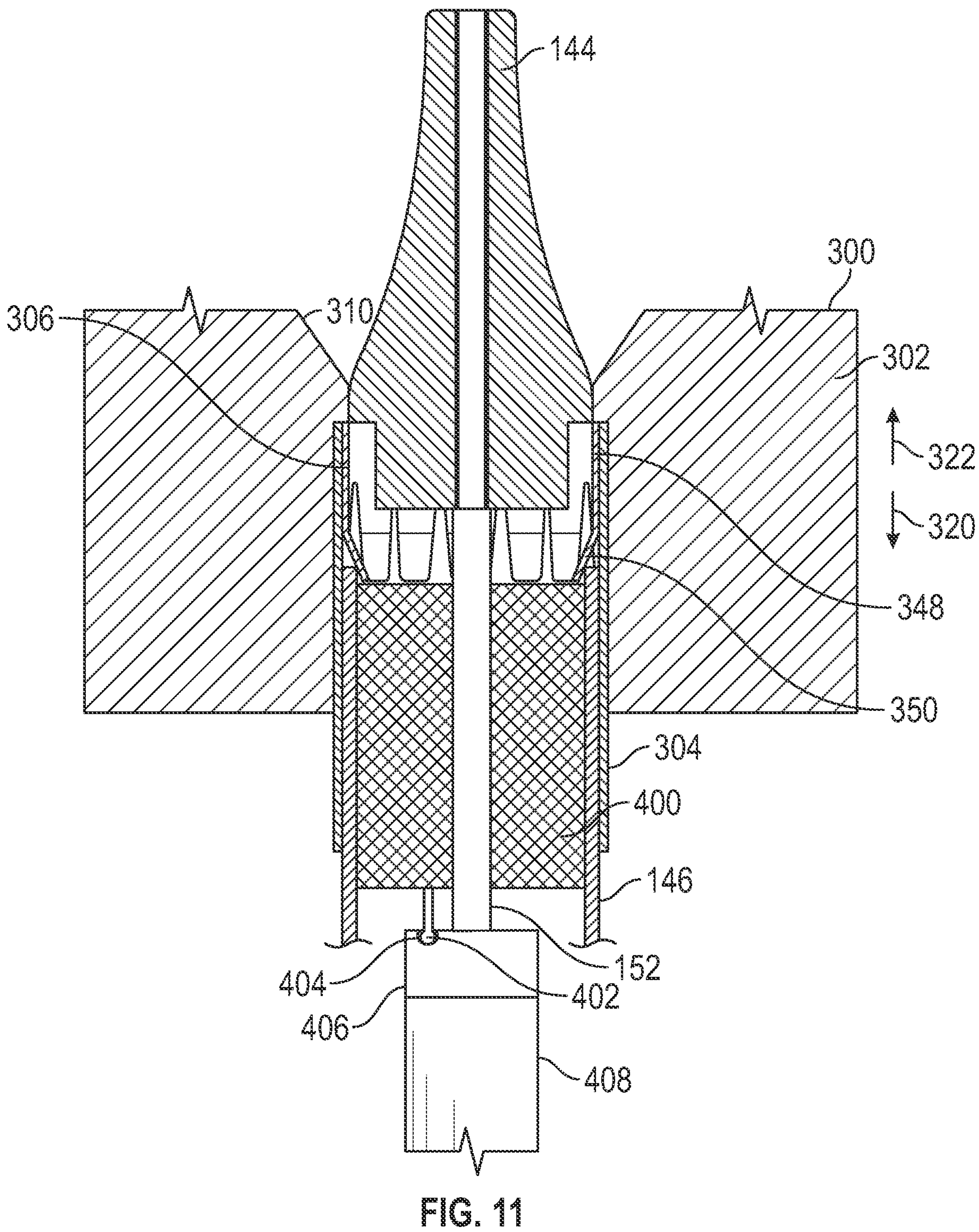
FIG. 11 is a cross-sectional side view of the capsule of the delivery apparatus arranged within the loading apparatus of FIG. 6, illustrating a prosthetic heart valve loaded into the capsule and a nosecone of the delivery apparatus arranged at a distal end of the loading apparatus.
Figure 12:
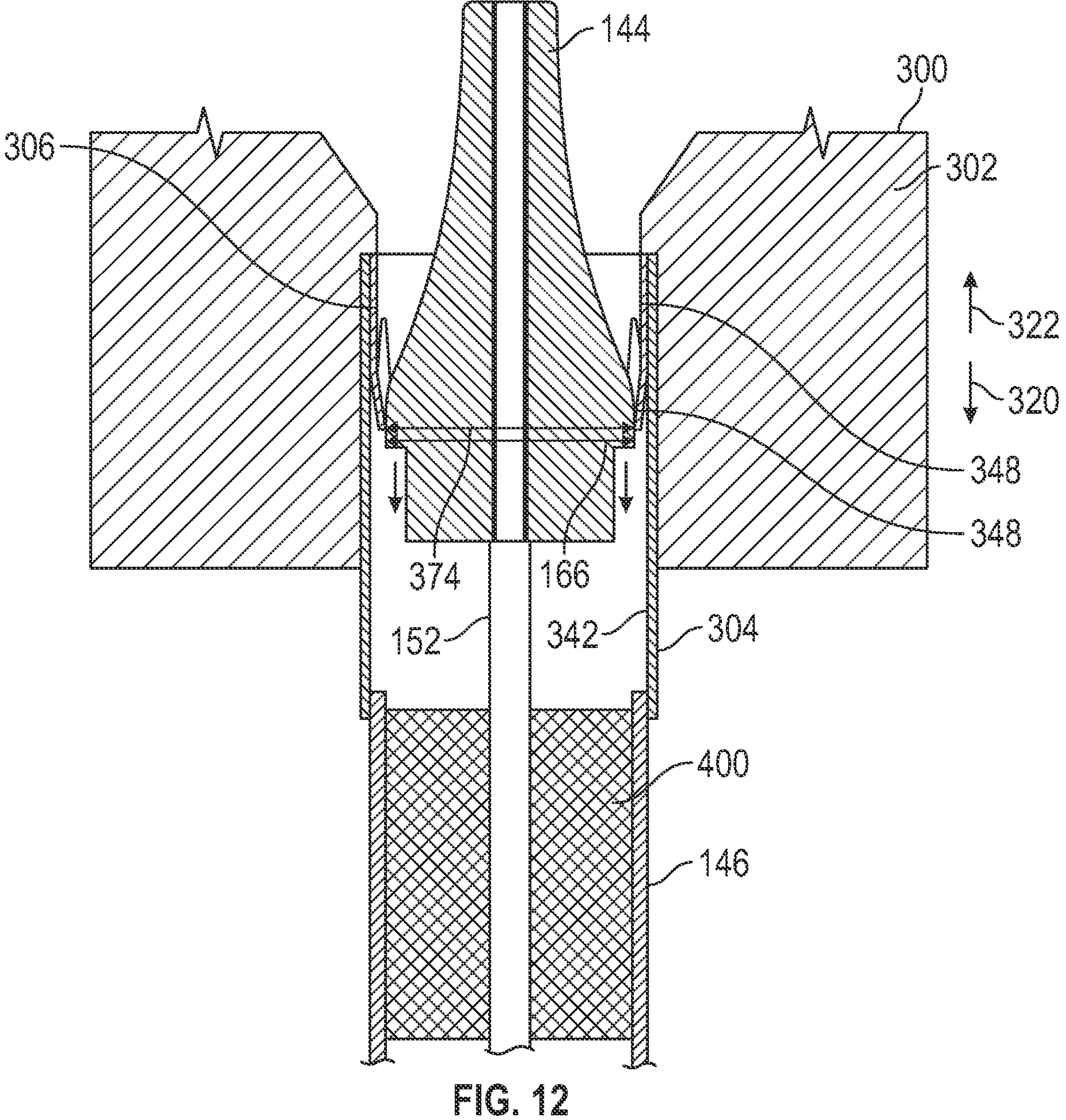
FIG. 12 is a cross-sectional side view of the loading apparatus of FIG. 6, illustrating pulling the nosecone of the delivery apparatus through the loading apparatus after loading the prosthetic heart valve into the capsule.

For example, in some embodiments, the loading member 306 can have a first (e.g., loading) configuration, as shown in FIGS. 7-11, where the proximal end 358 of each of the flexible arms 350 is angled (e.g., bent) radially inward relative to its corresponding distal end 356 (e.g., to a greater degree than when in the second configuration, as described further below). The loading member 306 can have a second (e.g., outwardly flexed) configuration, as shown in FIG. 12 (described further below), where the proximal ends (or proximal end portions) 358 of each of the flexible arms 350 are bent in a radially outward direction from the first configuration, in response to a force being applied to an interior surface of the flexible arms 350. In some embodiments, as shown in FIG. 12, in the second configuration, the proximal ends 358 are or are almost in line, in an axial direction relative to the central longitudinal axis 308, with the ring portion 348. When the applied force is removed (e.g., when the loader 300 is pulled away from the delivery apparatus and the nosecone is pulled out of the loading member 306, as described further below), the flexible arms 350 return to their first, loading configuration (which, in some embodiments, may be referred to as a resting configuration). In this way, the plurality of flexible arms 350 can resiliently flex radially outward in response to the application of a radially outward force and then return to their loading state (in which their proximal ends extend radially inward relative to the ring portion 348) when the applied, radially outward force is removed.

In other embodiments, the plurality of arms 350 are plastically deformable and are configured to flex from the first configuration to the second configuration and then remain in the radially outward, second configuration, even after the nosecone is removed from the loader.

In other embodiments, at least a portion of each arm of the plurality of arms 350 is removably coupled to a remainder of the loading member 306 and configured to break off from the remainder of the loading member 306 in response to a radially outward force, greater than a threshold, applied to an inner surface of the portion of the arm 350. For example, each arm 350 can include at least a portion, proximate to the proximal end 358 of the arm, that is connected to a remaining portion of the arm 350 (or the ring portion) via a separable connection (represented by line 357 in FIG. 9) that is configured to break under a force that is greater than a threshold. In some embodiments, the threshold is a non-zero threshold. In some embodiments, the threshold may be a minimum force applied to the inner surface of the arms 350 during pulling the nosecone through the loading member 306. In some embodiments, the separable connection, arranged along line 357, can include a score line and/or a perforation region (e.g., a line of perforations). In this way, the proximal end portion of each arm 350 may be configured to tear off along line 357, in response to a radially outward pressure applied to the inner surfaces of the arms 350 during pulling the nosecone through the loading member 306.

In still other embodiments, in the initial configuration (e.g., for loading of the valve), each arm of the plurality of arms 350 can be connected to adjacent arms 350 of the plurality of arms (e.g., connected along at least a portion of the edges between arms, as shown as slots between adjacent arms 350 in FIG. 9) by perforations or score lines. Then, in response to a radially outward force, as the nosecone is pushed through the loading member 306, the perforations or score lines between adjacent arms 350 may break, causing the arms 350 to break apart from one another around the circumference of the loading member and create a larger diameter opening at the proximal end of the loading member 306. As a result, the nosecone may pass through the loading member 306.

In some embodiments, the outer diameter 352 of the ring portion 348 of the loading member 306 is approximately the same, or slightly smaller than, the inner diameter 344 of the guide tube 304. As shown in FIGS. 7 and 8, the loading member 306 is arranged within the distal portion 336 of the guide tube 304. More specifically, a distal edge of the ring portion 348 is aligned with a distal end of the guide tube 304 and arranged proximate to the narrowed end of the conical bore 310. The arms 350 extend toward to the proximal end 314 of the outer body 302.

In this way, the distal portion 336 of the guide tube 304 is retained (e.g., disposed) between the cylindrical bore 316 of the outer body 302 and the loading member 306.

In some embodiments, the loading member 306 is rigidly attached to the guide tube 304, for example by welding the distal edge of the ring portion 348 to the distal end of the guide tube 304. As an example, as shown in FIG. 10, an outer surface of the distal edge of the ring portion 348 can be rigidly attached via a weld point 360 to an inner surface of the distal end of the guide tube 304. In alternate embodiments, the weld point 360 may instead be a point for an adhesive bond or another type of securing bond between the guide tube 304 and loading member 306. Further, in alternate embodiments, the weld point 360 may extend further along the mating surfaces of the ring portion 348 and the guide tube 304 than shown in FIG. 10 and/or the weld point 360 may be location at a different axial location along the mating surfaces of the ring portion 348 and the guide tube 304.

As introduced above, in some embodiments, one or more inner surfaces (radially inward facing) of the loader 300 can comprise a surface treatment or texture that is configured to reduce friction between the inner surface and an object sliding against and along the inner surface(s). For example, such surface treatments or textures can allow a prosthetic heart valve and/or nose cone sliding through an interior of the loader 300 to slide more easily with reduced friction.

Figure 14:
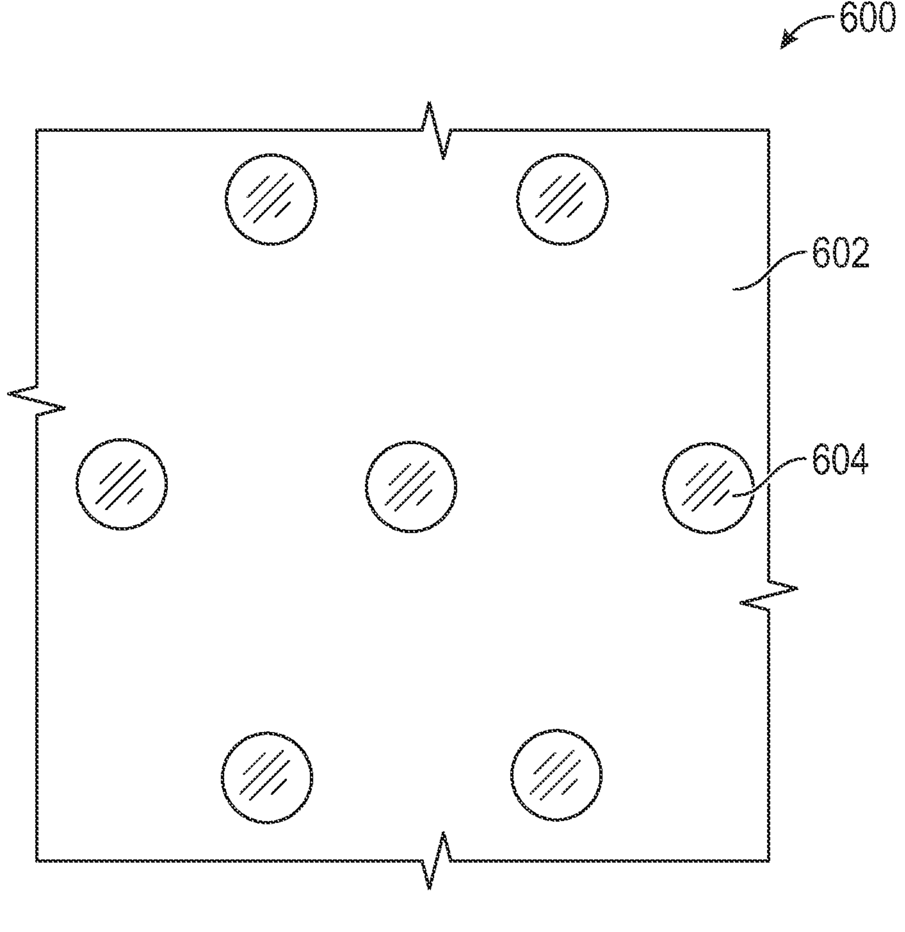
FIG. 14 is a schematic of a portion of an inner surface of the loading apparatus of FIG. 6, the inner surface including a surface treatment configured to reduce frictional surfaces between the inner surface and an object sliding along the inner surface.

FIG. 14 shows a schematic of a portion of a surface 600, which can be a portion of an inner surface (radially inward facing) of the loading apparatus 300, such as one of the inner surface 332 of the conical bore 310 and/or the inner surface 334 of the loading member 306. As shown in FIG. 14, the surface 600 includes a relatively smooth base surface 602 and a surface treatment configured to reduce frictional surfaces between the surface 600 and an object sliding against and along the surface 600. The surface treatment can comprise a plurality of protrusions or indentations 604 out of or into, respectively, the base surface 602 and spaced apart from one another along the surface 600, thereby creating a surface roughness to the surface 600 which is configured to reduce friction.

In some embodiments, the protrusions or indentations 604 can be protrusions configured as raised bumps or nubs that extend outward (radially outward) from the base surface 602 (e.g., toward a central longitudinal axis of the loader 300). In some embodiments, instead of circular protrusions, the protrusions 604 can be oblong or configured as raised waves or ribs spaced apart from one another across the surface 600.

In other embodiments, the protrusions or indentations 604 can be indentations (or depressions) configured as pits or dimples into the base surface 602. In other embodiments, instead of circular indentations 604, the indentations 604 can be oblong, wave-like, or channel-like indentations 604 spaced apart from one another across the surface 600.

The protrusions or indentations 604 can be created by molding (for a polymer material) or plastic deformation (for metal) of the material of the surface 600. Further, the protrusions or indentations 604 can be relatively small-scale, such as on the scale of micrometers, thereby creating a rough textured surface on the surface 600 which can reduce frictional forces between the surface 600 and another surface sliding against the surface 600.

FIG. 13 is a flow chart of an exemplary method 500 for loading a prosthetic heart valve into a capsule of a delivery apparatus using a loading apparatus. FIGS. 10-12 illustrate the exemplary method 500, using loader 300 to load a prosthetic heart valve 400 (which may, in some embodiments, be valve 10 of FIG. 1) into the capsule (capsule 146 of delivery apparatus 100 is used as an example). As described further below, the method 500 may include using the loader 300 to radially compress the at least partially, radially expanded prosthetic heart valve 400 and load the radially compressed prosthetic heart valve 400 into the capsule 146 of the delivery apparatus. The method 500 may then further include removing the loader 300 from the delivery apparatus by sliding the loader 300 distally away from the assembled delivery apparatus. Method 500 is described in more detail below, with reference to FIGS. 10-13.

As shown in FIG. 13, method 500 begins at 502 by arranging the capsule of the delivery apparatus in a guide tube of a loading apparatus (e.g., loader 300), so that a distal end of the capsule is arranged between, in a radial direction relative to a central longitudinal axis of the loading apparatus, an inner surface of the guide tube and an outer surface of a loading member of the loading apparatus, a ring portion of the loading member coupled to the inner surface of the guide tube, the guide tube including a distal portion arranged within an inner cylindrical bore of an outer body of the loading apparatus and a proximal portion extending outward, in an axial direction, from a proximal end of the outer body.

For example, as shown in FIG. 10, the capsule 146 of a delivery apparatus (e.g., delivery apparatus 100 of FIG. 2) is arranged inside the guide tube 304 of the loader 300. In some embodiments, the capsule 146 of the delivery apparatus can be slid in the distal direction 322, into the guide tube 304, such that the distal edge (or end) 160 of the capsule 146 is arranged between, in a radial direction relative to the central longitudinal axis 308 of the loader 300, an inner surface (e.g., lumen) 342 of the guide tube 304 and outer surfaces of the arms 350 of the loading member 306.

As shown in FIG. 10, in the absence of an external forces, the arms 350 of the loading member 306 are angled (e.g., bent) radially inward, toward the central longitudinal axis 308. This is referred to herein as the loading, first configuration of the loading member 306. In some embodiments, this may be referred to as a resting configuration of the loading member 306.

During insertion of the capsule 146 into the loader 300, when the capsule 146 reaches the arms 350 of the loading member 306, the distal edge 160 of the capsule 146 engages the outer surface of the proximal ends 358 of the arms 350 (as shown in FIG. 10). As a result, in some embodiments (e.g., when the arms are flexible arms), the arms 350 can be flexed (e.g., pressed) further radially inward, while the distal edge 160 of the capsule 146 is retained between the arms 350 and the guide tube 304. In alternate embodiments, the arms 350 may not flex further radially inward in response to engaging with the capsule 146.

In this position, the proximal end of the loading member 306, defined by the proximal ends 358 of the arms 350, has a first inner diameter 372, which is narrower than the inner diameter 168 of the capsule 146. Thus, the radially compressed prosthetic heart valve may be more easily loaded into the inner lumen of the capsule 146. In some embodiments, this configuration of the loading member may be the same as the first configuration. In alternate embodiments, in this configuration of the loading member, the proximal end of the loading member 306 may have a slightly smaller diameter than when in the first configuration, and thus, this configuration may be referred to as the loading configuration (while the first configuration is the resting configuration).

Returning to FIG. 13, method 500 continues to 504. The method at 504 includes sliding the prosthetic heart valve, in an at least partially radially expanded state, through an inner conical bore of the outer body of the loading apparatus, the conical bore extending from a distal end of the outer body to the cylindrical bore, the conical bore narrowing from a larger, first diameter at the distal end of the outer body to a smaller, second diameter at an entrance to the cylindrical bore, and radially compressing the prosthetic heart valve as is slides through the narrowing, conical bore.

For example, to load the prosthetic heart valve 400 into the capsule 146, as shown in FIG. 11, the prosthetic heart valve 400 can be slid, in the proximal direction 320 into and through the inner conical bore 310 of the outer body 302 of the loader 300. Since the conical bore 310 narrows in diameter, along an axial length of the conical bore 310, to the narrower, second diameter 328 (as shown in FIG. 10), the prosthetic heart valve 400 is radially compressed as it travels through the conical bore 310, toward the capsule 146.

Returning to FIG. 13, at 506, the method includes sliding the prosthetic heart valve through an interior of the loading member to further radially compress the prosthetic heart valve via a plurality of arms of the loading member that extend axially from the ring portion and are angled radially inward, toward the central longitudinal axis.

The method then continues to 508, which includes sliding the radially compressed prosthetic heart valve into the capsule.

For example, as shown in FIG. 10, since the arms 350 of the loading member 306 are angled inward, the prosthetic heart valve 400 is further radially compressed as it slides along the inner surface of the arms 350. The radially compressed prosthetic heart valve 400 is then slid into the capsule 146, as shown in FIG. 11.

In some embodiments, as shown in FIG. 11, the method at 508 can include pushing one or more connecting posts 402 of the prosthetic heart valve 400 (which, in some embodiments, may be similar to posts 24 of valve 10 of FIG. 1) into corresponding recesses 404 of a retainer arranged at an end of an interior shaft 408 of the delivery apparatus. As a result, the prosthetic heart valve 400 may be prevented from moving axially relative to the shaft 408 and can be moved within the capsule 46 to retain it in the radially compressed state.

Returning to FIG. 13, the method 500 proceeds to 510 which includes removing the loading apparatus from the delivery apparatus by sliding the loading apparatus distally away from the capsule and bending the plurality of arms radially outward as a nosecone of the delivery device is pulled through the loading member, the nosecone arranged distal to the capsule.

For example, as explained above with reference to FIGS. 2-4, the delivery apparatus can include a nosecone 144 arranged distal to the capsule 146. Thus, as shown in FIG. 11, after loading the prosthetic heart valve 400 into the capsule 146, the nosecone 144 can be arranged within the conical bore 310 or distal to the loader 300. The nosecone 144 is connected to the rest of the delivery apparatus via inner shaft 152, as explained above with reference to FIG. 2.

In order to remove the loader 300 from the delivery device (or remove the delivery device from inside of the loader 300), the nosecone 144 can be pulled through the loading member 306, as the loader 300 is slid in the distal direction 322, away from the capsule 146, as shown in FIG. 12.

As the nosecone 144 pushes and slides against the inner surface of the arms 350, in some embodiments, the arms 350 are bent (e.g., flexed) radially outward (from their initial, radially inward position), toward the inner surface 342 of the guide tube 304. In this bent, second configuration of the loading member 306 (shown in FIG. 12), the proximal end of the loading member 306, defined by the proximal ends 358 of the flexible arms 350, has a second inner diameter 374, which is wider than the first inner diameter shown in FIG. 10. This actively widened, second inner diameter 374 (e.g., widened by applied, radially outward pressure from the outer walls of the nosecone 144), allows for the nosecone 144 to pass through the interior of the loading member 306. As a result, the loader 300 can be moved away from the delivery apparatus.

In some embodiments, in the second configuration shown in FIG. 12, the proximal ends 358 of the arms 350 are almost in line, in the axial direction, with the ring portion 348. In some embodiments, the arms 350 can be pressed against the inner surface 342 of the guide tube 304 in response to the nosecone 144 passing through an interior of the loading member 306.

In other embodiments, instead of flexing radially outward toward inner surface of the inner cylindrical bore, at 510, the method can include breaking or tearing at least a proximal end portion of each arm off and away from a remainder of the loading member, in response to a pressure applied to the proximal end portions of the arms, as the nosecone is pulled through the loading member. As a result, a diameter of a proximal end of the loading member may be increased, thereby allowing the nosecone to pass through and out of the loader.

Thus, as shown in FIGS. 10-12, the narrowest, second diameter 328 of the conical bore 310 and the inner diameter 354 of the ring portion 348 of the loading member 306, are at least slightly larger than the maximal outer diameter 166 of the nosecone 144, and the arms 350 are able to flex radially outward to (or break off to result in) the diameter 374 which is equal to or larger than the maximal outer diameter 166 of the nosecone 144. As a result, the nosecone 144 can be pulled through the loader 300, such that the loader 300 may be fully removed from the delivery apparatus.

In some embodiments (e.g., when the arms are flexible arms), the method at 510 in FIG. 13 can further include, after removing the apparatus from the delivery apparatus, and the nosecone is no longer being pulled through the loading member, passively returning the plurality of flexible arms back to their loading (or resting) configuration where a diameter of a proximal end of the loading member, defined by proximal ends of the plurality of flexible arms, is smaller than a diameter of the proximal end of the loading member during pulling the nosecone through the plurality of flexible arms of the loading member. Passively returning the flexible arms back to their first configuration may include the flexible arms automatically (e.g., without the application of external force) flexing back to this resting configuration in response to the radially outward force (or pressure) applied to the arms via the nosecone being removed.

In this way, the loader 300 including a loading member with axially extending arms that can resiliently flex (or break off) from a radially inward state, defining a proximal diameter narrower than the inner diameter of the capsule, to a less radially inward state (or physically separated state), defining a diameter which is equal to or larger than the outer diameter of the nosecone, can allow for both easier valve loading and for removal of the loader from the delivery apparatus, by allowing the nosecone to be pulled through the loader.

Additional Examples of the Disclosed Technology

In view of the above described implementations of the disclosed subject matter, this application discloses the additional examples enumerated below. It should be noted that one feature of an example in isolation or more than one feature of the example taken in combination and, optionally, in combination with one or more features of one or more further examples are further examples also falling within the disclosure of this application.

Example 1. A loading apparatus, comprising: an outer body including an inner conical bore that narrows in diameter from a distal end to a proximal end portion of the outer body; a guide tube including a distal portion arranged within the proximal end portion of the outer body and a proximal portion extending outward from the outer body; and an annular loading member including a ring portion and a plurality of arms extending outward, in an axial direction relative to a central longitudinal axis of the loading apparatus, from the ring portion, the plurality of arms arranged around a circumference of the ring portion, the ring portion coupled to an inner surface of the distal portion of the guide tube.

Example 2. The loading apparatus of any example herein, particularly example 1, wherein the distal portion of the guide tube is arranged within a cylindrical bore of the proximal end portion of the outer body, the cylindrical bore extending from a narrowed end of the inner conical bore to a proximal end of the outer body.

Example 3. The loading apparatus of any example herein, particularly example 2, wherein the ring portion of the loading member is arranged within the guide tube, adjacent to where the inner conical bore transitions into the cylindrical bore.

Example 4. The loading apparatus of any example herein, particularly any one of examples 1-3, wherein the outer body further includes an inner cylindrical bore that extends from a narrowed end of the inner conical bore, within the proximal end portion, to a proximal end of the outer body.

Example 5. The loading apparatus of any example herein, particularly example 4, wherein the inner conical bore has a wider, first end arranged at the distal end of the outer body, where a smallest diameter of the first end is a first diameter, and a narrower, second end arranged at a transition between the inner conical bore and the inner cylindrical bore, wherein a smallest diameter of the second end is a second diameter, and wherein the inner cylindrical bore has a third diameter that is larger than the second diameter and smaller than the first diameter.

Example 6. The loading apparatus of any example herein, particularly example 5, wherein the first end and the second end of the conical bore have a circular shape.

Example 7. The loading apparatus of any example herein, particularly example 5, wherein the first end and the second end of the conical bore have an elliptical shape and the first diameter and the second diameter are minor axes of the first end and second end, respectively.

Example 8. The loading apparatus of any example herein, particularly any one of examples 5-7, wherein the transition is a step transition between the inner conical bore and the inner cylindrical bore.

Example 9. The loading apparatus of any example herein, particularly any one of examples 4-8, wherein the distal portion of the guide tube is arranged within the cylindrical bore.

Example 10. The loading apparatus of any example herein, particularly any one of examples 4-9, wherein the ring portion of the annular loading member has an inner, fourth diameter and proximal ends of the plurality of arms, when in a loading configuration, have an inner, fifth diameter that is smaller than the fourth diameter and smaller than the second diameter.

Example 11. The loading apparatus of any example herein, particularly example 10, wherein the fourth diameter and the second diameter are the same.

Example 12. The loading apparatus of any example herein, particularly any one of examples 1-11, wherein an inner surface of the inner conical bore and an inner surface of the annular loading member provides a continuous inner surface of the loading apparatus, in a direction of the central longitudinal axis.

Example 13. The loading apparatus of any example herein, particularly any one of examples 1-12, wherein each arm of the plurality of arms includes a wider, distal end attached to the ring portion and a narrower, proximal end that is spaced away from the ring portion, in the axial direction.

Example 14. The loading apparatus of any example herein, particularly example 13, wherein the proximal ends of the plurality of arms are spaced apart from one another, around a circumference of the loading member.

Example 15. The loading apparatus of any example herein, particularly any one of examples 13 and 14, wherein each arm is a flexible arm configured to flex radially outward, relative to the central longitudinal axis, from a loading, first configuration of the loading member to a flexed, second configuration of the loading member, wherein, in the first configuration, the proximal end of each flexible arm is angled radially inward from its corresponding distal end and the ring portion, and wherein, in the second configuration, the proximal end of each flexible arm is bent radially outward relative to the first configuration such that the proximal end is angled radially inward to a lesser degree than when in the first configuration.

Example 16. The loading apparatus of any example herein, particularly example 15, wherein an inner diameter of a proximal end of the loading member, formed by the proximal ends of the plurality of arms, is larger in the second configuration than the first configuration.

Example 17. The loading apparatus of any example herein, particularly any one of examples 13 and 14, wherein each arm includes at least a portion, proximate to the proximal end of the arm, that is connected to a remaining portion of the arm or the ring portion via a separable connection that is configured to break under a force that is greater than a threshold.

Example 18. The loading apparatus of any example herein, particularly example 17, wherein the separable connection includes one of a score line and a perforated line.

Example 19. The loading apparatus of any example herein, particularly any one of examples 1-18, wherein the plurality of arms comprises an elastically deformable material.

Example 20. The loading apparatus of any example herein, particularly any one of examples 1-19, wherein at least a portion of each arm of the plurality of arms is removably coupled to a remainder of the annular loading member and configured to break off from the remainder of the annular loading member in response to a radially outward force, greater than a threshold, applied to an inner surface of the portion of the arm.

Example 21. The loading apparatus of any example herein, particularly any one of examples 1-20, wherein the ring portion is coupled to the inner surface of the distal portion of the guide tube via a welded connection.

Example 22. The loading apparatus of any example herein, particularly any one of examples 1-21, wherein the guide tube and plurality of arms of the loading member are configured to receive a capsule of a delivery apparatus in a space between the inner surface of the guide tube and an outer surface of the plurality of arms, the capsule configured to receive a radially compressed prosthetic heart valve therein.

Example 23. A method for loading a prosthetic heart valve into a capsule of a delivery apparatus, comprising: arranging the capsule of the delivery apparatus in a guide tube of a loading apparatus, so that a distal end of the capsule is arranged between, in a radial direction relative to a central longitudinal axis of the loading apparatus, an inner surface of the guide tube and an outer surface of a loading member of the loading apparatus, a ring portion of the loading member coupled to the inner surface of the guide tube, the guide tube including a distal portion arranged within an inner cylindrical bore of an outer body of the loading apparatus and a proximal portion extending outward, in an axial direction, from a proximal end of the outer body; radially compressing the prosthetic heart valve by sliding the prosthetic heart valve through an inner conical bore of the outer body of the loading apparatus, the conical bore narrowing from a distal end of the outer body to the cylindrical bore, and by sliding the prosthetic heart valve through a plurality of arms of the loading member that extend axially outward from the ring portion and angle radially inward toward the central longitudinal axis; sliding the radially compressed prosthetic heart valve from the loading member into the capsule to load the prosthetic heart valve into the capsule; and removing the loading apparatus from the delivery apparatus by sliding the loading apparatus distally away from the capsule and bending the plurality of arms radially outward as a nosecone of the delivery device is pulled through the loading member, the nosecone arranged distal to the capsule.

Example 24. The method of any example herein, particularly example 23, wherein arranging the capsule in the guide tube includes sliding the capsule distally toward and into the guide tube and sliding the distal end of the capsule to engage an outer surface of the plurality of arms and flex the plurality of arms further radially inward during the sliding the prosthetic heart valve through the plurality of flexible arms.

Example 25. The method of any example herein, particularly any one of examples 23-24, wherein a diameter of a proximal end of the loading member, defined by proximal ends of the plurality of arms, is greater during removing the loading apparatus from the delivery apparatus, while pulling the nosecone through the loading member, than during sliding the prosthetic heart valve through the inner conical bore and the plurality of arms of the loading member.

Example 26. The method of any example herein, particularly any one of examples 23-25, wherein a diameter of a proximal end of the loading member, defined by proximal ends of the plurality of arms that are spaced away from the ring portion, in the axial direction, during sliding the prosthetic heart valve through the inner conical bore and through the plurality of arms, is smaller than a narrowest diameter of the inner conical bore, wherein a portion of the inner conical bore having the narrowest diameter is arranged adjacent to the ring portion of the loading member.

Example 27. The method of any example herein, particularly any one of examples 23-26, wherein during the radially compressing the prosthetic heart valve and sliding the radially compressed prosthetic heart valve into the capsule, the nosecone is arranged distally away from the cylindrical bore and the loading member.

Example 28. The method of any example herein, particularly any one of examples 23-27, wherein bending the plurality of arms radially outward as the nosecone is pulled through the loading member includes applying a radially outward force against an inner surface of the plurality of arms by an outer surface of the nosecone, as it is pulled through the loading member, and bending each arm of the plurality of arms toward the inner surface of the guide tube to widen an opening formed by proximal ends of the plurality of flexible arms.

Example 29. The method of any example herein, particularly any one of examples 23-28, wherein each arm of the plurality of arms is a flexible arm configured to flex under applied pressure.

Example 30. The method of any example herein, particularly example 29, further comprising, after removing the loading apparatus from the delivery apparatus, and the nosecone is no longer being pulled through the loading member, passively returning the plurality of flexible arms back to their resting configuration where a diameter of a proximal end of the loading member, defined by proximal ends of the plurality of flexible arms, is smaller than a diameter of the proximal end of the loading member during pulling the nosecone through the plurality of flexible arms of the loading member.

Example 31. The method of any example herein, particularly any one of examples 23-27, wherein bending the plurality of arms radially outward as the nosecone is pulled through the loading member includes applying a radially outward force against an inner surface of the plurality of arms by an outer surface of the nosecone, as it is pulled through the loading member, and breaking at least a proximal portion of each arm of the plurality of arms off from a remainder of the loading member in response to the radially outward force, to widen an opening formed at a proximal end of the loading member.

Example 32. A method for loading a prosthetic heart valve into a capsule of a delivery apparatus, comprising: arranging the capsule of the delivery apparatus in a guide tube of a loading apparatus, so that a distal end of the capsule is arranged between, in a radial direction relative to a central longitudinal axis of the loading apparatus, an inner surface of the guide tube and an outer surface of an annular loading member of the loading apparatus, a ring portion of the loading member coupled to the inner surface of the guide tube, the guide tube including a distal portion arranged within an inner cylindrical bore of an outer body of the loading apparatus and a proximal portion extending outward, in an axial direction, from a proximal end of the outer body; sliding a prosthetic heart valve, in an at least partially radially expanded state, through an inner conical bore of the outer body of the loading apparatus, the conical bore extending from a distal end of the outer body to the cylindrical bore, the conical bore narrowing from a larger, first diameter at the distal end of the outer body to a smaller, second diameter at an entrance to the cylindrical bore, and radially compressing the prosthetic heart valve as is slides through the narrowing, conical bore; sliding the prosthetic heart valve through an interior of the loading member to further radially compress the prosthetic heart valve via a plurality of flexible arms of the loading member that extend axially from the ring portion and are angled radially inward, toward the central longitudinal axis, the plurality of flexible arms arranged around a circumference of the ring portion, wherein proximal ends of the plurality of flexible arms are spaced away from one another around a circumference of the loading member and are configured to flex in a radial direction relative to the central longitudinal axis; and sliding the radially compressed prosthetic heart valve into the capsule.

Example 33. The method of any example herein, particularly example 32, further comprising removing the loading apparatus from the delivery apparatus by sliding the loading apparatus distally away from the capsule and bending the plurality of flexible arms radially outward as a nosecone of the delivery device is pulled through the loading member, the nosecone arranged distal to the capsule, in the axial direction.

Example 34. The method of any example herein, particularly example 33, wherein bending the plurality of flexible arms radially outward as the nosecone is pulled through the loading member includes applying a radially outward force against an inner surface of the plurality of flexible arms by an outer surface of the nosecone, as it is pulled through the loading member, and bending each arm of the plurality of flexible arms toward the inner surface of the guide tube to widen an opening formed by the proximal ends of the plurality of flexible arms.

Example 35. The method of any example herein, particularly any one of examples 33 and 34, further comprising, after removing the loading apparatus from the delivery apparatus, and the nosecone is no longer being pulled through the loading member, passively returning the plurality of flexible arms back to their resting configuration where a diameter of a proximal end of the loading member, defined by the proximal ends of the plurality of flexible arms, is smaller than a diameter of the proximal end of the loading member during pulling the nosecone through the plurality of flexible arms of the loading member.

Example 36. The method of any example herein, particularly any one of examples 33-35, wherein a diameter of a proximal end of the loading member, defined by the proximal ends of the plurality of flexible arms, is greater during removing the loading apparatus from the delivery apparatus, while pulling the nosecone through the loading member, than during sliding the prosthetic heart valve through the inner conical bore and the plurality of flexible arms of the loading member.

Example 37. The method of any example herein, particularly any one of examples 32-36, wherein arranging the capsule in the guide tube includes flexing the proximal ends of the plurality of flexible arms radially inward in response to the distal end of the capsule applying pressure against an outer surface of the plurality of flexible arms, in a radially inward direction, when arranged between the inner surface of the guide tube and the outer surface of the loading member.

Example 38. The method of any example herein, particularly any one of examples 32-37, wherein a diameter of a proximal end of the loading member, defined by the proximal ends of the plurality of flexible arms that are spaced away from the ring portion, in the axial direction, during sliding the prosthetic heart valve through the inner conical bore and through the interior of the loading member, is smaller than a narrowest diameter of the inner conical bore, wherein a portion of the inner conical bore having the narrowest diameter is arranged adjacent to the ring portion of the loading member.

Example 39. The method of any example herein, particularly any one of examples 32-38, wherein during the sliding the prosthetic heart valve through the interior of the loading member and into the capsule, the nosecone is arranged distally away from the cylindrical bore and the loading member.

Example 40. The method of any example herein, particularly any one of examples 32-39, wherein sliding the radially compressed prosthetic heart valve into the capsule includes pushing one or more connecting posts of the prosthetic heart valve into corresponding recesses of a retainer arranged at an end of an interior shaft of the delivery apparatus.

Example 41. A loading apparatus, comprising: an outer body including an inner conical bore and an inner cylindrical bore that are continuous with one another along a length of the outer body, the conical bore narrowing in diameter from a distal end of the outer body to the cylindrical bore and the cylindrical bore extending from a narrowed end of the conical bore to a proximal end of the outer body; a guide tube including a distal portion arranged within the cylindrical bore and a proximal portion extending outward from the proximal end of the outer body; and an annular loading member including a ring portion and a plurality of flexible arms arranged around a circumference of the loading member, the plurality of flexible arms extending outward, in an axial direction relative to a central longitudinal axis of the loading apparatus, from the ring portion, the ring portion coupled to an inner surface of the distal portion of the guide tube, and wherein proximal ends of the plurality of flexible arms, arranged away from the ring portion, are angled radially inward toward the central longitudinal axis when the annular loading member is in a loading, first configuration.

Example 42. The loading apparatus of any example herein, particularly example 41, wherein in the loading, first configuration, an inner diameter formed by the proximal ends of the plurality of flexible arms is smaller than an inner diameter of the ring portion.

Example 43. The loading apparatus of any example herein, particularly example 42, wherein each flexible arm of the plurality of flexible arms is configured to bend radially outward from the loading, first configuration, to a flexed, second configuration where the proximal end of each flexible arm is arranged closer to the inner surface of the guide tube than when in the first configuration, in response to a radially outward force applied to an inner surface of the plurality of flexible arms.

Example 44. The loading apparatus of any example herein, particularly example 43, wherein, in the second configuration, the inner diameter formed by the proximal ends of the plurality of flexible arms increases relative to the inner diameter formed by the proximal ends of the plurality of flexible arms when in the first configuration.

Example 45. The loading apparatus of any example herein, particularly any one of examples 43 and 44, wherein, in the second configuration, the inner diameter formed by the proximal ends of the plurality of flexible arms is the same as the inner diameter of the ring portion.

Example 46. The loading apparatus of any example herein, particularly any one of examples 41-45, wherein each flexible arm of the plurality of flexible arms includes a wider, distal end attached to the ring portion and a narrower, proximal end that is spaced away from the ring portion, in the axial direction.

Example 47. The loading apparatus of any example herein, particularly example 46, wherein the proximal ends of the plurality of flexible arms are spaced apart from one another, around a circumference of the loading member.

Example 48. The loading apparatus of any example herein, particularly any one of examples 46 and 47, wherein each flexible arm is configured to flex radially outward, relative to the central longitudinal axis, from the first configuration to a flexed, second configuration of the loading member, wherein, in the first configuration, the proximal end of each flexible arm is angled radially inward from its corresponding distal end and the ring portion, and wherein, in the second configuration, the proximal end of each flexible arm is bent radially outward relative to the first configuration such that the proximal end is angled radially inward to a lesser degree than when in the first configuration.

Example 49. The loading apparatus of any example herein, particularly example 48, wherein an inner diameter of a proximal end of the loading member, formed by the proximal ends of the plurality of flexible arms, is larger in the second configuration than in the first configuration.

Example 50. The loading apparatus of any example herein, particularly any one of examples 41-49, wherein the plurality of flexible arms comprises an elastically deformable material.

Example 51. The loading apparatus of any example herein, particularly any one of examples 41-50, wherein the ring portion is coupled to the inner surface of the distal portion of the guide tube via a welded connection.

Example 52. The loading apparatus of any example herein, particularly any one of examples 41-51, wherein the conical bore has a wider, first diameter at the distal end of the outer body and a narrower, second diameter at a transition between the conical bore and the cylindrical bore, and wherein the cylindrical bore has a third diameter that is larger than the second diameter and smaller than the first diameter.

Example 53. The loading apparatus of any example herein, particularly example 52, wherein the transition is a step transition between the conical bore and the cylindrical bore.

Example 54. The loading apparatus of any example herein, particularly any one of examples 52 and 53, wherein the ring portion of the annular loading member has an inner, fourth diameter and proximal ends of the plurality of flexible arms, when in the loading, first configuration, have an inner, fifth diameter that is smaller than the fourth diameter and smaller than the second diameter.

Example 55. The loading apparatus of any example herein, particularly example 54, wherein the fourth diameter and the second diameter are the same.

Example 56. The loading apparatus of any example herein, particularly any one of examples 41-55, wherein an inner surface of the conical bore and an inner surface of the annular loading member provides a continuous inner surface of the loading apparatus, in a direction of the central longitudinal axis.

Example 57. The loading apparatus of any example herein, particularly any one of examples 41-56, wherein the guide tube and plurality of flexible arms of the loading member are configured to receive a capsule of a delivery apparatus in a space between the inner surface of the guide tube and an outer surface of the plurality of flexible arms, the capsule configured to receive a radially compressed prosthetic heart valve therein.

In view of the many possible embodiments to which the principles of the disclosed technology may be applied, it should be recognized that the illustrated embodiments are only preferred examples of the disclosed technology and should not be taken as limiting the scope of the claimed subject matter. Rather, the scope of the claimed subject matter is defined by the following claims and their equivalents.

I claim:

1. A loading apparatus, comprising:

an outer body including an inner conical bore that narrows in diameter from a distal end to a proximal end portion of the outer body;

a guide tube including a distal portion arranged within the proximal end portion of the outer body and a proximal portion extending outward from the outer body; and an annular loading member including a ring portion and a plurality of axially extending arms extending from the ring portion, wherein the plurality of arms are arranged around a circumference of the ring portion, the ring portion coupled to an inner surface of the distal portion of the guide tube.

2. The loading apparatus of claim 1, wherein the distal portion of the guide tube is arranged within a cylindrical bore of the proximal end portion of the outer body, the cylindrical bore extending from a narrowed end of the inner conical bore to a proximal end of the outer body, and wherein the ring portion of the loading member is arranged within the guide tube, adjacent to where the inner conical bore transitions into the cylindrical bore.

3. The loading apparatus of claim 1, wherein the outer body further includes an inner cylindrical bore that extends from a narrowed end of the inner conical bore, within the proximal end portion, to a proximal end of the outer body, wherein the inner conical bore has a wider, first end arranged at the distal end of the outer body and a narrower, second end arranged at a transition between the inner conical bore and the inner cylindrical bore, wherein a smallest diameter of the first end is a first diameter, wherein a smallest diameter of the second end is a second diameter, and wherein the inner cylindrical bore has a third diameter that is larger than the second diameter and smaller than the first diameter.

4. The loading apparatus of claim 3, wherein the transition is a step transition between the inner conical bore and the inner cylindrical bore.

5. The loading apparatus of claim 3, wherein the ring portion of the loading member has an inner, fourth diameter and proximal ends of the plurality of arms, when in a loading configuration, have an inner, fifth diameter that is smaller than the fourth diameter and smaller than the second diameter.

6. The loading apparatus of claim 5, wherein the fourth diameter and the second diameter are the same.

7. The loading apparatus of claim 1, wherein an inner surface of the inner conical bore and an inner surface of the loading member provides a continuous inner surface of the loading apparatus, in a direction of the central longitudinal axis, and comprises a surface roughness configured to reduce friction.

8. The loading apparatus of claim 1, wherein each arm of the plurality of arms includes a wider, distal end attached to the ring portion and a narrower, proximal end that is spaced away from the ring portion, in the axial direction and wherein the proximal ends of the plurality of arms are spaced apart from one another, around a circumference of the loading member.

9. The loading apparatus of claim 8, wherein each arm is a flexible arm configured to flex radially outward, relative to a central longitudinal axis of the loading apparatus, from a loading, first configuration of the loading member to a flexed, second configuration of the loading member, wherein in the first configuration the proximal end of each flexible arm is angled radially inward from its corresponding distal end and the ring portion, and wherein in the second configuration the proximal end of each flexible arm is bent radially outward relative to the first configuration such that the proximal end is angled radially inward to a lesser degree than when in the first configuration.

10. The loading apparatus of claim 9, wherein an inner diameter of a proximal end of the loading member, formed by the proximal ends of the plurality of arms, is larger in the second configuration than the first configuration.

11. The loading apparatus of claim 8, wherein each arm includes at least a portion, proximate to the proximal end of the arm, that is connected to a remaining portion of the arm or the ring portion via a separable connection that is configured to break under a force that is greater than a threshold.

12. The loading apparatus of claim 1, wherein the guide tube and plurality of arms of the loading member are configured to receive a capsule of a delivery apparatus in a space between the inner surface of the guide tube and an outer surface of the plurality of arms, the capsule configured to receive a radially compressed prosthetic heart valve therein.

13. A loading apparatus, comprising:

an outer body including an inner conical bore and an inner cylindrical bore that are continuous with one another along a length of the outer body, the conical bore narrowing in diameter from a distal end of the outer body to the cylindrical bore and the cylindrical bore extending from a narrowed end of the conical bore to a proximal end of the outer body;

a guide tube including a distal portion arranged within the cylindrical bore and a proximal portion extending outward from the proximal end of the outer body; and an annular loading member including a ring portion and a plurality of flexible arms arranged around a circumference of the loading member, the plurality of flexible, axially extending arms extending from the ring portion, wherein the ring portion is coupled to an inner surface of the distal portion of the guide tube, wherein each flexible arm has a distal end arranged at the ring portion and a proximal end arranged away from the ring portion, and wherein the proximal end of each flexible arm is angled radially inward toward a central longitudinal axis of the loading apparatus when the loading member is in a loading, first configuration.

14. The loading apparatus of claim 13, wherein in the loading, first configuration, an inner diameter formed by the proximal ends of the plurality of flexible arms is smaller than an inner diameter of the ring portion and wherein each flexible arm of the plurality of flexible arms is configured to bend radially outward from the loading, first configuration, to a flexed, second configuration where the proximal end of each flexible arm is arranged closer to the inner surface of the guide tube than when in the first configuration, in response to a radially outward force applied to an inner surface of the plurality of flexible arms.

15. The loading apparatus of claim 14, wherein, in the second configuration, the inner diameter formed by the proximal ends of the plurality of flexible arms increases relative to the inner diameter formed by the proximal ends of the plurality of flexible arms when in the first configuration.

16. The loading apparatus of claim 13, wherein the plurality of flexible arms comprises an elastically deformable material.

17. The loading apparatus of claim 13, wherein the guide tube and plurality of flexible arms of the loading member are configured to receive a capsule of a delivery apparatus in a space between the inner surface of the guide tube and an outer surface of the plurality of flexible arms, the capsule configured to receive a radially compressed prosthetic heart valve therein.

* * * * *